United States Patent
Jung et al.

(10) Patent No.: US 10,857,139 B2
(45) Date of Patent: Dec. 8, 2020

(54) SUBSTITUTED DIAZASPIROALKANES AS ANDROGEN RECEPTOR MODULATORS

(71) Applicant: The Regents of the University of California, Oakland, CA (US)

(72) Inventors: Michael E. Jung, Los Angeles, CA (US); Charles L. Sawyers, New York, NY (US); Samedy Ouk, Los Angeles, CA (US); Chris Tran, New York, NY (US); John Wongvipat, New York, NY (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/969,147

(22) Filed: May 2, 2018

(65) Prior Publication Data

US 2018/0318276 A1 Nov. 8, 2018

Related U.S. Application Data

(63) Continuation of application No. 15/181,030, filed on Jun. 13, 2016, now Pat. No. 9,987,261, which is a continuation of application No. 14/318,234, filed on Jun. 27, 2014, now Pat. No. 9,388,159, which is a continuation of application No. 13/615,085, filed on Sep. 13, 2012, now Pat. No. 8,802,689, which is a continuation of application No. 12/294,881, filed as application No. PCT/US2007/007485 on Mar. 27, 2007, now Pat. No. 8,445,507.

(60) Provisional application No. 60/833,790, filed on Jul. 28, 2006, provisional application No. 60/785,978, filed on Mar. 27, 2006.

(51) Int. Cl.
 *C07D 235/02* (2006.01)
 *A61K 31/4439* (2006.01)
 *C07D 401/04* (2006.01)
 *A61K 9/48* (2006.01)

(52) U.S. Cl.
 CPC ........... *A61K 31/4439* (2013.01); *A61K 9/48* (2013.01); *C07D 401/04* (2013.01)

(58) Field of Classification Search
 CPC .................................................. C07D 235/02
 USPC .................................................... 548/302.7
 See application file for complete search history.

(56) References Cited

U.S. PATENT DOCUMENTS

| | | |
|---|---|---|
| 3,823,240 A | 7/1974 | Sauli |
| 3,984,430 A | 10/1976 | Curran |
| 4,097,578 A | 6/1978 | Perronnet et al. |
| 4,234,736 A | 11/1980 | Bernauer et al. |
| 4,304,782 A | 12/1981 | Dumont et al. |
| 4,312,881 A | 1/1982 | Wooten |
| 4,399,216 A | 8/1983 | Axel et al. |
| 4,407,814 A | 10/1983 | Bernauer et al. |
| 4,427,438 A | 1/1984 | Nagano et al. |
| 4,473,393 A | 9/1984 | Nagpal |
| 4,482,739 A | 11/1984 | Bernauer et al. |
| 4,559,157 A | 12/1985 | Smith et al. |
| 4,608,392 A | 8/1986 | Jacquet et al. |
| 4,749,403 A | 6/1988 | Liebl et al. |
| 4,820,508 A | 4/1989 | Wortzman |
| 4,859,228 A | 8/1989 | Prisbylla |
| 4,873,256 A | 10/1989 | Coussediere et al. |
| 4,938,949 A | 7/1990 | Borch et al. |
| 4,944,791 A | 7/1990 | Schroder et al. |
| 4,992,478 A | 2/1991 | Geria |
| 5,010,182 A | 4/1991 | Brake et al. |
| 5,069,711 A | 12/1991 | Fischer et al. |
| 5,071,773 A | 12/1991 | Evans et al. |
| 5,166,358 A | 11/1992 | Seuron et al. |
| 5,411,981 A | 5/1995 | Gaillard-Kelly et al. |
| 5,434,176 A | 7/1995 | Claussner et al. |
| 5,554,607 A | 9/1996 | Elokdah et al. |
| 5,556,983 A | 9/1996 | Claussner et al. |
| 5,589,497 A | 12/1996 | Claussner et al. |
| 5,614,620 A | 3/1997 | Liao et al. |
| 5,627,201 A | 5/1997 | Gaillard-Kelly et al. |
| 5,646,172 A | 7/1997 | Claussner et al. |
| 5,656,651 A | 8/1997 | Sovak et al. |
| 5,705,654 A | 1/1998 | Claussner et al. |

(Continued)

FOREIGN PATENT DOCUMENTS

| | | |
|---|---|---|
| AU | 217893 | 6/1958 |
| CN | 101032483 A | 9/2007 |

(Continued)

OTHER PUBLICATIONS

Jordan, V. C. Nature Reviews: Drug Discovery, 2, 2003, 205.*

(Continued)

*Primary Examiner* — Douglas M Willis

(74) *Attorney, Agent, or Firm* — Anson M. Nomura; Mintz, Levin, Cohn, Ferris, Glovsky and Popeo, P.C.

(57) ABSTRACT

Provided herein are compounds and pharmaceutical compositions including the compound having a formula:

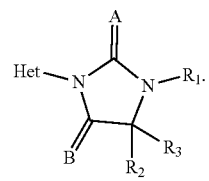

These compounds are androgen receptor modulators useful for the treatment of androgen receptor-associated conditions.

15 Claims, 6 Drawing Sheets

(56) References Cited

U.S. PATENT DOCUMENTS

| | | | |
|---|---|---|---|
| 5,726,061 | A | 3/1998 | Robbins et al. |
| 5,750,553 | A | 5/1998 | Claussner et al. |
| 5,783,707 | A | 7/1998 | Elokdah et al. |
| RE35,956 | E | 11/1998 | Gaillard-Kelly et al. |
| 5,958,936 | A | 9/1999 | Claussner et al. |
| 5,985,868 | A | 11/1999 | Gray |
| 6,107,488 | A | 8/2000 | Bouchet et al. |
| 6,172,076 | B1 | 1/2001 | Embrey et al. |
| 6,235,910 | B1 | 5/2001 | Beller et al. |
| 6,242,611 | B1 | 6/2001 | Claussner et al. |
| 6,307,030 | B1 | 10/2001 | French et al. |
| 6,350,763 | B1 | 2/2002 | Kelly et al. |
| 6,472,415 | B1 | 10/2002 | Sovak et al. |
| 6,479,063 | B2 | 11/2002 | Weisman et al. |
| 6,489,163 | B1 | 12/2002 | Roy et al. |
| 6,506,607 | B1 | 1/2003 | Shyjan |
| 6,828,471 | B2 | 12/2004 | Sawyers et al. |
| 7,271,188 | B2 | 9/2007 | Tachibana et al. |
| 8,445,507 | B2 | 5/2013 | Jung et al. |
| 8,802,689 | B2 | 8/2014 | Jung et al. |
| 9,388,159 | B2 | 7/2016 | Jung et al. |
| 9,987,261 | B2 | 6/2018 | Jung et al. |
| 2002/0133833 | A1 | 9/2002 | Sawyers et al. |
| 2003/0225138 | A1 | 12/2003 | Sircar et al. |
| 2004/0009969 | A1 | 1/2004 | Cleve et al. |
| 2004/0116417 | A1 | 6/2004 | Boubia et al. |
| 2005/0153968 | A1 | 7/2005 | Bi et al. |
| 2006/0025589 | A1 | 2/2006 | Binet et al. |
| 2006/0127902 | A1 | 6/2006 | Madden et al. |
| 2007/0249697 | A1 | 10/2007 | Tachibana et al. |

FOREIGN PATENT DOCUMENTS

| | | | |
|---|---|---|---|
| DE | 2102605 | | 7/1971 |
| DE | 2614831 | A1 | 10/1977 |
| EP | 0 017 976 | A2 | 10/1980 |
| EP | 0 017 976 | A3 | 10/1980 |
| EP | 0 017 976 | B1 | 10/1980 |
| EP | 0 002 259 | B1 | 10/1984 |
| EP | 0144098 | A1 | 6/1985 |
| EP | 0 331 232 | | 9/1989 |
| EP | 362179 | | 4/1990 |
| EP | 0 494 819 | A1 | 1/1992 |
| EP | 0 494 819 | B1 | 1/1992 |
| EP | 0 578 516 | A1 | 5/1993 |
| EP | 0 580 459 | A1 | 5/1993 |
| EP | 0 580 459 | B1 | 5/1993 |
| EP | 0572 191 | A1 | 12/1993 |
| EP | 0770613 | A1 | 5/1995 |
| EP | 0 721 944 | B1 | 1/2001 |
| EP | 1 790 640 | A1 | 5/2007 |
| FR | 2 693 461 | | 1/1994 |
| FR | 2 715 402 | | 1/1994 |
| FR | 2 845 384 | | 10/2002 |
| FR | 2 845 385 | A1 | 4/2004 |
| FR | 2 845 385 | B1 | 4/2004 |
| GB | 800244 | A | 8/1958 |
| JP | 59210083 | A | 11/1984 |
| JP | 60-239737 | | 11/1985 |
| JP | 1009978 | A | 1/1989 |
| JP | 2019363 | A | 1/1990 |
| JP | 08-09997 | A | 5/2008 |
| WO | WO-1990/013646 | | 11/1990 |
| WO | WO-1997/000071 | | 1/1997 |
| WO | WO-1997/019064 | | 5/1997 |
| WO | WO-1997/019931 | | 6/1997 |
| WO | WO-2000/017163 | | 3/2000 |
| WO | WO-2000/026195 | A1 | 5/2000 |
| WO | WO-2000/044731 | A1 | 8/2000 |
| WO | WO-2001/007048 | A1 | 2/2001 |
| WO | WO-2001/092253 | A2 | 12/2001 |
| WO | WO-2001/094346 | A1 | 12/2001 |
| WO | WO-2002/053155 | A1 | 7/2002 |
| WO | WO-2002/081453 | A1 | 10/2002 |
| WO | WO-2003/029245 | A1 | 4/2003 |
| WO | WO-2003/032994 | A2 | 4/2003 |
| WO | WO-2003/057220 | A1 | 7/2003 |
| WO | WO-2003/093243 | A1 | 11/2003 |
| WO | WO-2003/096980 | A2 | 11/2003 |
| WO | WO-2003/096980 | A3 | 11/2003 |
| WO | WO-2004/022572 | A1 | 3/2004 |
| WO | WO-2004/030633 | A2 | 4/2004 |
| WO | WO-2004/030633 | A3 | 4/2004 |
| WO | WO-2004/031160 | A2 | 4/2004 |
| WO | WO-2004/070050 | A2 | 8/2004 |
| WO | WO-2004/111031 | A1 | 12/2004 |
| WO | WO-2005/042488 | A1 | 5/2005 |
| WO | WO-2005/059109 | A2 | 6/2005 |
| WO | WO-2005/059109 | A3 | 6/2005 |
| WO | WO-2005/060661 | | 7/2005 |
| WO | WO-2005/089752 | A2 | 9/2005 |
| WO | WO-2005/089752 | A3 | 9/2005 |
| WO | WO-2005/099693 | | 10/2005 |
| WO | WO-2006/010642 | A1 | 2/2006 |
| WO | WO-2006/028226 | A1 | 3/2006 |
| WO | WO-2006/124118 | A1 | 11/2006 |
| WO | WO-2007/045877 | A1 | 4/2007 |
| WO | WO-2007/126765 | A2 | 11/2007 |
| WO | WO-2007/126765 | A3 | 11/2007 |
| WO | WO-2007/127010 | | 11/2007 |
| WO | WO-2008/119015 | A2 | 10/2008 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Office Action dated Aug. 15, 2012 in Japanese Application No. 2009-502925, 5 pages. (English Translation).

Office Action dated Oct. 15, 2013 in Japanese Application No. 2012-27792, 13 pages. (English Translation).

A Textbook of Drug Design and Development, P. Krogsgaard-Larson and H. Bundgaard, eds. Ch 5, pp. 113-191 (Harwood Academic Publishers, 1991).

A.M. Soto et al., Control of Cell Proliferation: Evidence for Negative Control on Estrogen-sensitive T47D Human Breast Cancer Cells , Cancer Research, 46, (1986), pp. 2271-2275.

Abstract submitted by Samedy Ouk, Prostate Cancer Foundation Scientific Retreat, Scottsdale, Arizona, Sep. 29-Oct. 1, 2005.

Anonymous (Jan. 1, 2016). "The Pharmaceutics and Compounding Laboratory," retrieved from <http://pharmlabs.unc.edu/labs/powders/classification.htm>, last visited Aug. 19, 2016, 2 pages.

Ausubel et al., Current Protocols in Molecular Biology, Wiley Interscience Publishers, (1995).

Baek, S.H. et al. Exchange of N-CoR corepressor and Tip60 coactivator complexes links gene expression by NF-kappaB and beta-amyloid precursor protein. Cell 110, 55-67 (2002).

Balk, S.P. Androgen receptor as a target in androgen-independent prostate cancer. Urology 60, 132-8; discussion 138-9 (2002).

Batch,J.A., et al., "Androgen receptor gene mutations identified by SSCP in fourteen subjects with androgen insensitivity syndrome", Hum. Mol. Genet 1 (7), 497-503 (1992).

Bohl et al., "Structural basis for antagonism and resistance of bicalutamide in prostate cancer", Proc. Nat. Acad. Sci., 2005, v. 102(17), pp. 6201-6206.

Bredenberg, S. et al. (Jan. 1, 2003). "New Concepts in Administration of Drugs in Tablet Form," Comprehensive Summaries of Uppsala Dissertations from the Faculty of Pharmacy ACTA Universitatis Upsaliensis Uppsala, 83 pages.

Brockschmidt,F.F., et al., "The two most common alleles of the coding GGN repeat in the androgen receptor gene cause differences in protein function", J. Mol. Endocrinol. 39 (1), 1-8 (2007).

Burnstein et al. Androgen Glucocorticoid Regulation of Androgen Receptor cDNA Expression. Molecular and Cellular Endocrinology. 1995. v. 115, pp. 177-186.

C.D. Chen et al., "Molecular determinants of resistance to antiandrogen therapy", Nature Medicine, vol. 10, No. 1 (Jan. 2004) pp. 33-39.

Cai,C., et al., "c-Jun has multiple enhancing activities in the novel cross talk between the androgen receptor and Ets variant gene 1 in prostate cancer", Mol. Cancer Res. 5(7), 725-735 (2007).

(56) References Cited

OTHER PUBLICATIONS

Chang et al., Science 240 (4850), 324-326 (1988).
Chen, C.D., Welsbie, D.S., Iran, C., Baek, S.H., Chen, R., Vessella, R., Rosenfeld, M.G., and Sawyers, C.L., Molecular determinants of resistance to antiandrogen therapy, Nat. Med., 10: 3339, 2004.
Cinar et al. Androgen Receptor Mediates the Reduced Tumor Growth, Enhanced Androgen Responsiveness, and Selected Target Gene Transactivation in Human Prostate Cancer Cell Line. *Cancer Research*. 2001. v. 61. pp. 7310-7317.
Clegg, N.J. et al. (Mar. 15, 2012, e-published Jan. 20, 2012). "ARN-509: a novel antiandrogen for prostate cancer treatment," *Cancer Res* 72(6):1494-1503.
Cousty-Berlin, et al., "Preliminary Pharmacokinetics and Metabolism of Novel Nonsteroidal Antiandrogens in the Rat: Relation of their Systemic Activity to the Formation of a Common Metabolite," *J. Steroid Biochem. Molec. Biol.*, vol. 51, No. 1/2, pp. 47-55 (1994).
Craft, N. et al. Evidence for clonal outgrowth of androgen-independent prostate cancer cells from androgen-dependent tumors through a two-step process. Cancer Res 59,5030-6 (1999).
Craft, N., Shostak, Y., Carey, M. & Sawyers, C.L. A mechanism for hormone-independent prostate cancer through modulation of androgen receptor signaling by the HER-2/neutyrosine kinase. Nat Med 5, 280-5 (1999).
Deprimo, S.E. et al. Transcriptional programs activated by exposure of human prostate cancer cells to androgen. Genome Biol 3, Research0032 (2002).
Design of Prodrugs, edited by H. Bundgaard, (Elsevier, 1985).
Dhal, P.N. et al., "Synthesis of thiohydantoins, thiazolidones and their derivatives from $N^1$-(4'-aryl thiazole 2-YL) thioureas", J. Indian Chem. Soc. 50(1):680-684, Oct. 1973.
Edwards, J., Krishna, N.S., Grigor, K.M. & Bartlett, J.M. Androgen receptor gene amplification and protein expression in hormone refractory prostate cancer. Br J Cancer 89, 552-6 (2003).
Ellis, W.J. et al. Characterization of a novel androgen-sensitive, prostate-specific antigen-producing prostatic carcinoma xenograft: LuCaP 23. Clin Cancer Res 2, 1039-48 (1996).
Ellwood-Yen, K. et al. Myc-driven murine prostate cancer shares molecular features with human prostate tumors. Cancer Cell 4, 223-38 (2003).
Elokdah, Hassan, et al., "Design, synthesis, and biological evaluation of thio-containing compounds with serum HDL-cholesterol-elevating properties", J. Med. Chem. 47:681-695 (2004).
European Search Report dated Jul. 20, 2011 for European Application No. 07754060.7, 7 pages.
Extended European Search Report dated Jul. 12, 2011 for European Application No. 11163948.0, 10 pages.
Extended European Search Report issued in European Patent Application No. EP 06748863.5, dated Feb. 12, 2009.
Feher, et al., "BHB: A Simple Knowledge-Based Scoring Function to Improve the Efficiency of Database Screening," *J. Chem. Inf. Comput. Sci.*, vol. 43, pp. 1316-1327 (2003).
Feldman, B.J. & Feldman, D. The development of androgen-independent prostate cancer. Nat Rev Cancer 1, 34-45 (2001).
Font De Mora, J. & Brown, M. AIB1 is a conduit for kinase-mediated growth factor signaling to the estrogen receptor. Mol Cell Biol 20, 5041-7 (2000).
Foury, et al., "Control of the Proliferation of Prostate Cancer Cells by an Androgen and Two Antiandrogens. Cell Specific Sets of Responses," *J. Steroid Biochem. Molec. Biol.*, vol. 66, No. 4, pp. 235-240 (1998).
Gelmann, E.P. Molecular biology of the androgen receptor. J Clin Oncol 20, 3001-15 (2002).
Gioeli, D. et al. Androgen receptor phosphorylation. Regulation and identification of the phosphorylation sites. J Biol Chem 277, 29304-14 (2002).
Glass, C.K. & Rosenfeld, M.G. The coregulator exchange in transcriptional functions of nuclear receptors. Genes Dev 14, 121-41 (2000).
Goubet, et al., Conversion of a Thiohydantoin to he Corresponding Hydantoin via a Ring-Opening/Ring Closure Mechanism, *Tetrahedron Letters*, vol. 37, No. 43, pp. 7727-7730 (1996).
Grad, J.M., Dai, J.L., Wu, S. & Burnstein, K.L. Multiple androgen response elements and a Myc consensus site in the androgen receptor (AR) coding region are involved in androgen-mediated up-regulation of AR messenger RNA. Mol Endocrinol 13, 1896-911 (1999).
Graham and Van Der Eb, "A new technique for the assay of infectivity of human adenovirus 5 DNA", Virology, v. 52(2) (Apr. 1973) pp. 456-467.
Gregory, C.W. et al. A mechanism for androgen receptor-mediated prostate cancer recurrence after androgen deprivation therapy. Cancer Res 61, 4315-9 (2001).
Gregory, C.W., Johnson, R.T., Jr., Mohler, J.L., French, F.S. & Wilson, E.M. Androgen receptor stabilization in recurrent prostate cancer is associated with hypersensitivity to low androgen. Cancer Res 61, 2892-8 (2001).
Hamilton-Reeves, J.M., et al, Isoflavone-rich soy protein isolate suppresses androgen receptor expression without altering estrogen receptor-beta expression or serum hormonal profiles in men at high risk of prostate cancer, J. Nutr. 137 (7), 1769-1775 (2007).
Homma, S., et al., Differential levels of human leukocyte antigen-class I, multidrug-resistance 1 and androgen receptor expressions in untreated prostate cancer cells: the robustness of prostate cancer, Oncol. Rep. 18 (2), 343-346 (2007).
Horoszewicz, J.S. et al. LNCaP model of human prostatic carcinoma. Cancer Res 43, 1809-18 (1983).
Huang, Z.Q., Li, J. & Wong, J. AR possess an intrinsic hormone-independent transcriptional activity. Mol Endocrinol 16, 924-37 (2002).
International Search Report issued in International Application No. PCT/US2007/007854, dated Apr. 15, 2008.
International Search Report issued in International Application No. PCT/US2008/012149 dated Apr. 29, 2009.
International Search Report issued in PCT Application No. PCT/US2004/042221, dated Jun. 20, 2005.
International Search Report issued in PCT Application PCT/US2005/005529, dated Nov. 10, 2005.
International Search Report issued in PCT Application PCT/US2007/07485, dated Sep. 4, 2008.
J. Holzbeierlein et al., "Gene Expression Analysis of Human Prostate Carcinoma during Hormonal Therapy Identifies Androgen-Responsive Genes and Mechanisms of Therapy Resistance", Am. J. Pathology, vol. 164, No. 1 (Jan. 2004) pp. 217-227.
Jones, *Genetics*, 85:12 (1977).
Karp et al., "Prostate Cancer Prevention: Investigational Approaches and Opportunities", Cancer Res., v. 56 (Dec. 15, 1996) pp. 5547-5556.
Karvonen, et al., "Interaction of Androgen Receptors with Androgen Response Element in Intact Cells," *The Journal of Biological Chemistry*, vol. 272, No. 25, pp. 15973-15979 (1997).
Kato, S. et al. Activation of the estrogen receptor through phosphorylation by mitogen-activated protein kinase. Science 270, 1491-4 (1995).
Kemppainen, et al., "Distinguishing Androgen Receptor Agonists and Antagonists: Distinct Mechanisms of Activation by Medroxyprogesterone Acetate and Dihydrotestosterone," *Mol. Endocrinol.*, vol. 13, pp. 440-454 (1999); mend.endojournals.org.
Keown et al., *Methods in Enzymology*, 185:527-537 (1990).
Kingsman et al., *Gene*, 7: 141 (1979).
Kinoshita, H. et al. Methylation of the androgen receptor minimal promoter silences transcription in human prostate cancer. Cancer Res 60, 3623-30 (2000).
Klein, K.A. et al. Progression of metastatic human prostate cancer to androgen independence in immunodeficient SCID mice. Nat Med 3, 402-8 (1 9 9 7).
Kousteni, S. et al. Nongenotropic, sex-nonspecific signaling through the estrogen or androgen receptors: dissociation from transcriptional activity. Cell 104, 719-30 (2001).

(56) References Cited

OTHER PUBLICATIONS

Laitinen, S., Karhu, R., Sawyers, C.L., Vessella, R.L. & Visakorpi, T. Chromosomal aberrations in prostate cancer xenografts detected by comparative genomic hybridization. Genes Chromosomes Cancer 35, 66-73 (2002).
Li, P. et al. Heterogeneous expression and functions of androgen receptor co-factors in primary prostate cancer. Am J Pathol 161, 1467-74 (2002).
Lobaccaro, J.M. et al. Molecular modeling and in vitro investigations of the human androgen receptor DNA-binding domain: application for the study of two mutations. Mol Cell Endocrinol 116, 137-47 (1 9 96).
Lu et al., "Molecular Mechanisms of Androgen-Independent Growth of Human Prostate Cancer LNCaP-AI Cells", Endocrinology 1999, vol. 140, No. 11, pp. 5054-5059.
M.J. Linja et al., Amplification and overexpression of androgen receptor gene in hormone-refractory prostate cancer, Cancer Research, vol. 61 (May 1, 2001) pp. 3550-3555.
Mammalian Cell Biotechnology: a Practical Approach, M. Butler, ed. (IRL Press, 1991).
Manolagas, S.C., Kousteni, S. & Jilka, R.L. Sex steroids and bone. Recent Prog Horm Res 57, 385-409 (2002).
Mansour et al., Nature, 336:348-352 (1988).
Marhefka, et al., "Homology Modeling Using Multiple Molecular Dynamics Simulations and Docking Sudies of the Human Androgen Receptor Ligand Binding Domain Bound to Testosterone and Nonsteroidal Ligands," J. Med. Chem., vol. 44, No. 11, pp. 1729-1740 (2001).
Masiello, D., Cheng, S., Bubley, G.J., Lu, M.L. & Balk, S.P. Bicalutamide functions as an androgen receptor antagonist by assembly of a transcriptionally inactive receptor. J Biol Chem 277, 26321-6 (2002).
Matias, et al., "Local Inhibition of Sebaceous Gland Growth by Topically Applied RU 58841," NY Acad. Sci., vol. 761, pp. 56-65 (1995).
Matias, P.M. et al. Structural basis for the glucocorticoid response in a mutant human androgen receptor (AR(ccr)) derived from an androgen-independent prostate cancer. J Med Chem 45, 143946 (2002).
Matias, P.M. et al. Structural evidence for ligand specificity in the binding domain of the human androgen receptor. Implications for pathogenic gene mutations. J Biol Chem 275, 26164-71 (2000).
McDonnell, T.J. et al. Expression of the protooncogene bcl-2 in the prostate and its association with emergence of androgen-independent prostate cancer. Cancer Res 52, 6940-4 (1992).
Migliaccio, A. et al. Steroid-induced androgen receptor-oestradiol receptor beta-Src complex triggers prostate cancer cell proliferation. Embo J 19, 5406-17 (2000).
Muller et al., 1991, Mol. & Cell. Bio. 11:1785.
Nam et al., Action of the Src Family Kinase Inhibitor, Dasatinib (BMS-354825), on Human Prostate Cancer Celle, Cancer Res., 2005, v. 65(20), pp. 9185-9189.
Navone, N. M., et al., "Model Systems of Prostate Cancer: Uses and Limitations" Cancer Metastasis, Kluwer Academic Publishers, Dordrecht, NL, 17 (4), 1999, pp. 361-371.
NM_000044<http://www.ncbi.nlm.nih.gov:80/entrez/viewerfcqi?cmd=Retrieve&db=nucleotide&list uids=21322251&dopt=GenBank&term=sapiens+AR-Fandrogen-Freceptor+prostate+cancer&qty=1>gi:21322251, printed Oct. 24, 2007.
Norris, J.D. et al. Peptide antagonists of the human estrogen receptor. Science 285, 744-6 (1999).
Notice of References Cited of Jul. 24, 1992 from U.S. Patent and Trademark Office for U.S. Appl. No. 07/819,110.
Office Action issued in U.S. Appl. No. 10/590,445, dated Mar. 2, 2009.
Office Action dated Jan. 18, 1994 from U.S. Patent and Trademark Office for U.S. Appl. No. 08/064,257.
Office Action dated Feb. 22, 1993 from U.S. Patent and Trademark Office for U.S. Appl. No. 07/819,110.
Office Action dated Jun. 1, 1994 from U.S. Patent and Trademark Office for U.S. Appl. No. 07/819,110.
Office Action dated Jul. 23, 2008 from U.S. Patent and Trademark Office for U.S. Appl. No. 10/590,445.
Office Action dated Aug. 11, 2009 from U.S. Patent and Trademark Office for U.S. Appl. No. 10/583,280.
Office Action dated Aug. 14, 1992 from U.S. Patent and Trademark Office for U.S. Appl. No. 07/819,110.
Office Action dated Sep. 2, 1993 from U.S. Patent and Trademark Office for U.S. Appl. No. 07/819,110.
P.J. Creaven et al., "Pharmacokinetics and Metabolism of Nilutamide", Supp. Urology, vol. 37, No. 2 (Feb. 1991) pp. 13-19.
Perou, C.M. et al. Molecular portraits of human breast tumors. Nature 406, 747-52 (2000).
Presentation of Charles Sawyers, Prostate Cancer Foundation Scientific Retreat, Scottsdale, Arizona, Sep. 29-Oct. 1, 2005.
Raffo, A.J. et al. Overexpression of bcl-2 Protects Prostate Cancer Cells from Apoptosis in Vitro and Confers Resistance to Androgen Depletion in Vivo. Cancer Research 55. 1995. v. 55. 44384445.
Remington: The Science and Practice of Pharmacy, 19th Edition, Gennaro (ed.) 1995, Mack Publishing Company, Easton, PA.
S.Ouk et al., Development of Androgen Receptor Inhibitors for Hormone-refractory Prostate Cancer, Prostate Cancer Foundation Meeting, Scottsdale, AZ, Sep. 29-Oct. 1, 2005.
Sack, J.S. et al. Crystallographic structures of the ligand-binding domains of the androgen receptor and its T877A mutant complexed with the natural agonist dihydrotestosterone. Proc Natl Acad Sci U S A 98, 4904-9 (2001).
Sambrook et al., Molecular Cloning: A Laboratory Manual 2nd edition (1989) Cold Spring Harbor Laboratory Press, Cold Spring Harbor, NY.
Saunders, P.T., et al., "Point mutations detected in the androgen receptor gene of three men with partial androgen insensitivity syndrome", Clin. Endocrinol. (Oxf) 37 (3), 214-220 (1992).
Schellhammer, P.F. et al. Prostate specific antigen decreases after withdrawal of antiandrogen therapy with bicalutamide or flutamide in patients receiving combined androgen blockade. J Urol 157, 1731-5 (1997).
Sderholm, et al., "Three-Dimensional Structure-Activity Relationships of Nonsteroidal Ligands in Complex with Androgen Receptor Ligand-Binding Domain," J. Med. Chem., vol. 48, No. 4, pp. 917-925 (2005).
Shang, Y. & Brown, M. Molecular determinants for the tissue specificity of SERMs. Science 295, 2465-8 (2002).
Shang, Y., Myers, M. & Brown, M. Formation of the androgen receptor transcription complex. Mol Cell 9, 601-10 (2002).
Shi, Xu-Bao, et al., Functional analysis of 44 mutant androgen receptors from human prostate cancer, Cancer Research 62 (5), pp. 1496-1502 (Mar. 1, 2002).
Shiau, A.K. et al. The structural basis of estrogen receptor/coactivator recognition and the antagonism of this interaction by tamoxifen. Cell 95, 927-37 (1998).
Singh et al., "Androgen Receptor Antagonists (Antiandrogens): Structure-Activity Relationships", Current Medicinal Chemistry, 2000, 7, pp. 211-247.
Sperry, et al., Androgen binding profiles of two distinct nuclear androgen receptors in Atlantic croaker (Micropogonias undulates), Journal of Steroid Biochemistry & Molecular Biology, vol. 73, pp. 93-103 (2000).
Stinchcomb et al., Nature, 282:39 (1979).
Su, Q.R., et al., "Polymorphisms of androgen receptor gene in childhood and adolescent males with first-onset major depressive disorder and association with related symptomatology", Int. J. Neurosci. 117 (7), 903-917 (2007).
Sweet, C.R., et al., "A unique point mutation in the androgen receptor gene in a family with complete androgen insensitivity syndrome", Fertil. Steril. 58 (4), 703-707 (1992).
Szelei et al. Androgen-Induced Inhibition of Proliferation in Human Breast Cancer MCF7 Cells Transfected with Androgen Receptor. Endocrinology. 1997. v. 138 (4). pp. 1406-1412.
Taplin, M.E. et al. Androgen receptor mutations in androgen-independent prostate cancer: Cancer and Leukemia Group B Study 9663. J Clin Oncol 21, 2673-8 (2003).

(56) References Cited

OTHER PUBLICATIONS

Taplin, M.E. et al. Mutation of the androgen-receptor gene in metastatic androgen-independent prostate cancer. N Engl J Med 332, 1393-8 (1995).
Taplin, M.E. et al. Selection for androgen receptor mutations in prostate cancers treated with androgen antagonist. Cancer Res 59, 2511-5 (1999).
Teutsch, G.; Goubet, F.; Battmann, T.; Bonfils, A.; Bouchoux, F.; Cerede, E.; Gofflo, D.; Gaillard-Kelly, M.; Philibert. D. .*J. Steroid Biochem. Molec. Biol.* 1994, 48, 111-119.
*The Pharmacological Basis of Therapeutics*, Goodman and Gilman, eds., Macmillan Publishing Co., New York, 1941.
The Practice of Medicinal Chemistry, Camille G. Wermuth et al., Ch 31, (Academic Press, 1996).
Tremblay, A., Tremblay, G.B., Labrie, F. & Giguere, V. Ligand-independent recruitment of SRC-1 to estrogen receptor beta through phosphorylation of activation function AF-1. Mol Cell 3, 513-9 (1999).
Tschumper et al., *Gene*, 10: 157 (1980).
Urlaub et al., *Proc. Natl. Acad. Sci. USA*, 77:4216 (1980).
Van Dort, M. E.; Robins, D. M.; Wayburn, B. *J. Med. Chem.* 2000, 43, 3344-3347.
Veldscholte, J. et al. A mutation in the ligand binding domain of the androgen receptor of human LNCaP cells affects steroid binding characteristics and response to anti-androgens. Biochem Biophys Res Commun 173, 534-40 (1990).
Visakorpi, T. et al. In vivo amplification of the androgen receptor gene and progression of human prostate cancer. Nat Genet 9, 401-6 (1995).
Wainstein, M.A. et al. CWR22: androgen-dependent xenograft model derived from a primary human prostatic carcinoma. Cancer Res 54, 6049-52 (1994).
Wallen et al., "Angroden Receptor Gene Mutations in Hormone-Refractory Prostate Cancer", J. Pathology 1999, vol. 189, pp. 559-563.
Wang, Long G., et al., "Overexpressed androgen receptor linked to p21WAF1 silencing may be responsible for androgen independence and resistance to apoptosis of a prostate cancer cell line", Cancer Research 61 (20), pp. 7544-7551 (Oct. 15, 2001).
Wang, S. et al. Prostate-specific deletion of the murine Pten tumor suppressor gene leads to metastatic prostate cancer. Cancer Cell 4, 209-21 (2003).
Wermuth, Camille G., "Molecular Variations Based on Isosteric Replacements", *The Practice of Medicinal Chemistry*, 1996, 13:203-237.
Wooster, R., et al., "A germline mutation in the androgen receptor gene in two brothers with breast cancer and Reifenstein syndrome", Nat. Genet. 2 (2), 132-134 (1992).
Written Opinion issued in International Application No. PCT/US2007/007854, dated Apr. 15, 2008.
Written Opinion issued in International Application No. PCT/US2008/012149, dated Apr. 29, 2009.
Written Opinion issued in PCT Application No. PCT/US2004/042221, dated Jun. 20, 2005.
Written Opinion issued in PCT Application No. PCT/US2005/005529, dated Nov. 10, 2005.
Written Opinion issued in PCT Application No. PCT/US2006/011417, dated Jul. 3, 2006.
Written Opinion issued in PCT Application PCT/US2007/07485, dated Sep. 4, 2008.
Zarghami, et al., "Steroid hormone regulation of prostate-specific antigen gene expression in breast cancer," *British Journal of Cancer*, vol. 75, No. 4, pp. 579-588 (1997).
Zhau, H.Y. et al. Androgen-repressed phenotype in human prostate cancer. Proc Natl Acad Sci U S A 93,15152-7 (1996).
Zhou, Z.X., Sar, M., Simental, J.A., Lane, M.V. & Wilson, E.M. A ligand-dependent bipartite nuclear targeting signal in the human androgen receptor. Requirement for the DNA-binding domain and modulation by NH2-terminal and carboxyl-terminal sequences. J Biol Chem 269, 13115-23 (1994).
Zoppi, S., et al. " Amino acid substitutions in the DNA-binding domain of the human androgen receptor are a frequent cause of receptor-binding positive androgen resistance", Mol. Endocrinol. 6 (3), 409-415 (1992).
Zheng, Q. et al. (2000). "Synthesis and Nonlinear Optical Properties of p-(Dimethylamino) benzylidene Dyes Containing Different Acceptors," *Chemistry Letters* 29(12):1426-1427.

\* cited by examiner

SUBSTITUTED DIAZASPIROALKANES AS ANDROGEN RECEPTOR MODULATORS

CROSS-REFERENCES TO RELATED APPLICATIONS

This application is a continuation of U.S. Pat. No. 15,181,030, filed Jun. 13, 2016, which issued as U.S. Pat. No. 9,987,261 on Jun. 5, 2018, which is a continuation of U.S. patent application Ser. No. 14/318,234, filed Jun. 27, 2014, which issued as U.S. Pat. No. 9,388,159 on Jul. 12, 2016, which is a continuation of U.S. patent application Ser. No. 13/615,085, filed Sep. 13, 2012, which issued as U.S. Pat. No. 8,802,689 on Aug. 12, 2014, which is a continuation of U.S. patent application Ser. No. 12/294,881, filed Sep. 16, 2010, which issued as U.S. Pat. No. 8,445,507 on May 21, 2013, which is a U.S. National Phase Application under 35 U.S.C. § 371 of International Application No. PCT/US2007/007485, filed Mar. 27, 2007, which in turn claims the benefit of U.S. Provisional Patent Application No. 60/785,978, filed Mar. 27, 2006, and U.S. Provisional Patent Application No. 60/833,790, filed Jul. 28, 2006, all of which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under grant no. CA092131, awarded by the National Institutes of Health. The government has certain rights in the invention.

FIELD OF THE INVENTION

The present invention relates to hydantoins, thiohydantoins, dithiohydantoins, hydantoinimines and thiohydantoinimines compounds, methods of using such compounds in the treatment of androgen receptor-associated conditions, such as age-related diseases, for example, prostate cancer, and to pharmaceutical compositions containing such compounds.

BACKGROUND OF THE INVENTION

Prostate cancer is the most common incidence of cancer and the second leading cause of cancer death in Western men. When the cancer is confined locally, the disease can be cured by surgery or radiation. However, 30% of such cancer relapses with distant metastatic disease and others have advanced disease at diagnoses. Advanced disease is treated by castration and/or administration of anti-androgens, the so-called androgen deprivation therapy. Castration lowers the circulating levels of androgens and reduces the activity of androgen receptor (AR). Administration of anti-androgens blocks AR function by competing away androgen binding and therefore reduces the AR activity. Although initially effective, these treatments quickly fail and the cancer becomes hormone refractory.

Recently, overexpression of AR has been identified and validated as a cause of hormone refractory prostate cancer (*Nat. Med*, 2004, 10, 33-39). Overexpression of AR is sufficient to cause progression from hormone sensitive to hormone refractory prostate cancer, suggesting that better AR inhibitors than the current drugs can slow the progression of prostate cancer. It was demonstrated that AR and its ligand binding are necessary for growth of hormone refractory prostate cancer, indicating that AR is still a target for this disease. It was also demonstrated that overexpression of AR converts anti-androgens from antagonists to agonists in hormone refractory prostate cancer (an AR antagonist inhibits AR activity and an AR agonist stimulates AR activity). Data from this work explain why castration and anti-androgens fail to prevent prostate cancer progression and reveals un-recognized properties of hormone refractory prostate cancer.

Bicalutarnide (Brand name: Casodex) is the most commonly used anti-androgen. While it has inhibitory effect on AR in hormone sensitive prostate cancer, it fails to suppress AR when the cancer becomes hormone refractory. Two weaknesses of current antiandrogens are blamed for the failure to prevent prostate cancer progression from hormone sensitive stage to hormone refractory disease and to effectively treat hormone refractory prostate cancer. One is their weak antagonistic activities and the other is their strong agonistic activities when AR is overexpressed in hormone refractory prostate cancer. Therefore, better AR inhibitors with more potent antagonistic activities and minimal agonistic activities are needed to delay disease progression and to treat the fatal hormone refractory prostate cancer.

Nonsteroidal anti-androgens, have been preferred over steroidal compounds for prostate cancer because they are more selective and have fewer side effects. A wide variety of such compounds were described in U.S. Pat. Nos. 4,097,578, 5,411,981, and 5,705,654, U.S. published applications 2004/0009969 and 2007/0004753, and PCT international applications published as WO 97/00071, WO 00/17163 and WO 06/124118.

Accordingly, identification of compounds which have high potency to antagonize the androgen activity, and which have minimal agonistic activity would overcome the hormone refractory prostate cancer (HRPC) and avoid or slow-down the progression of hormone sensitive prostate cancer (HSPC). There is a need in the art for the identification of selective modulators of the androgen receptor, such as modulators which are non-steroidal, non-toxic, and tissue selective.

SUMMARY OF THE INVENTION

A series of compounds that modulate the function of the nuclear hormone receptors, especially the androgen receptor are presented. These compounds can cause disappearance of prostate cancer cells and tumors.

In an embodiment, a compound is according to formula II.

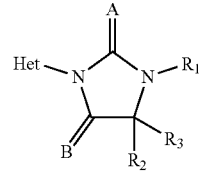

Formula II

Het represents a heterocyclic unit of 5 or 6 atoms. A and B are independently selected from oxygen, sulfur, and N—$R_9$, with $R_9$ being selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}$ (CS)$R_{11}$, NH(CS)NR$_{11}$R$_{12}$, or NR$_{12}$(CS)OR$_{11}$. $R_{11}$ and $R_{12}$ are independently selected from hydrogen, alkyl, substituted alkyl, alkenyl or substituted alkenyl, alkynyl or substituted alkynyl, aryl, substituted aryl, arylalkyl, arylalkenyl, arylalkynyl, heterocyclic aromatic or non-aromatic, or substituted heterocyclic aromatic or non-aromatic. $R_1$ is selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, SO$_2$R$_{11}$, NR$_{11}$R$_{12}$, NR$_{12}$(CO)OR$_{11}$, NH(CO)NR$_{11}$R$_{12}$, NR$_{12}$(CO)R$_{11}$, O(CO)R$_{11}$, O(CO)OR$_{11}$, O(CS)R$_{11}$, NR$_{12}$(CS)R$_{11}$, NH(CS)NR$_{11}$R$_{12}$, or NR$_{12}$(CS)OR$_{11}$. $R_2$ and $R_3$ are independently selected from hydrogen, aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, or substituted cycloalkyl, or, together with the carbon to which they are linked, form a cycle which can be cycloalkyl, substituted cycloalkyl, heterocyclic aromatic or non-aromatic, substituted heterocyclic aromatic or non-aromatic.

$R_1$ and $R_2$ can be connected to form a cycle which can be heterocyclic aromatic or non aromatic, substituted heterocyclic aromatic or non aromatic. $R_{11}$ and $R_{12}$ can be connected to form a cycle which can be heterocyclic aromatic or non-aromatic, substituted heterocyclic aromatic, cycloalkyl, or substituted cycloalkyl.

For example, the compound can be A51 or A52.

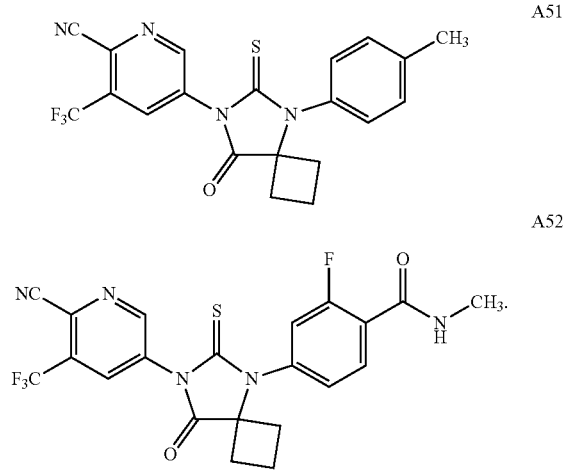

In an embodiment, a pharmaceutical composition includes a therapeutically effective amount of a compound according to Formula II, or a pharmaceutically acceptable salt thereof, and a pharmaceutically acceptable carrier, diluent, or adjuvant.

The pharmaceutical composition can include a solution of dimethylsulfoxide, phosphate buffered saline solution, and water. The pharmaceutical composition can include dimethylsulfoxide, a carboxymethylcellulose, a polysorbate, and water.

An embodiment of a method includes preventing or treating a disease or disorder related to nuclear receptor activity.

A method for preventing or treating a hyperproliferative disorder, such as hormone sensitive prostate cancer or hormone refractory prostate cancer, can include administering a compound according to Formula II, or a pharmaceutically acceptable salt thereof, to a subject in need of such prevention or treatment, thereby preventing or treating the hyperproliferative disorder. The compound can be administered at a dosage in the range of from about 1 mg per kg body weight per day to about 50 mg per kg body weight per day. The compound can be administered, for example, by intravenous injection, by injection into tissue, intraperitoneally, orally, or nasally.

In an embodiment, the compound according to Formula II is an antagonist of a nuclear receptor or an antagonist of an androgen receptor.

DETAILED DESCRIPTION

Figure 1:
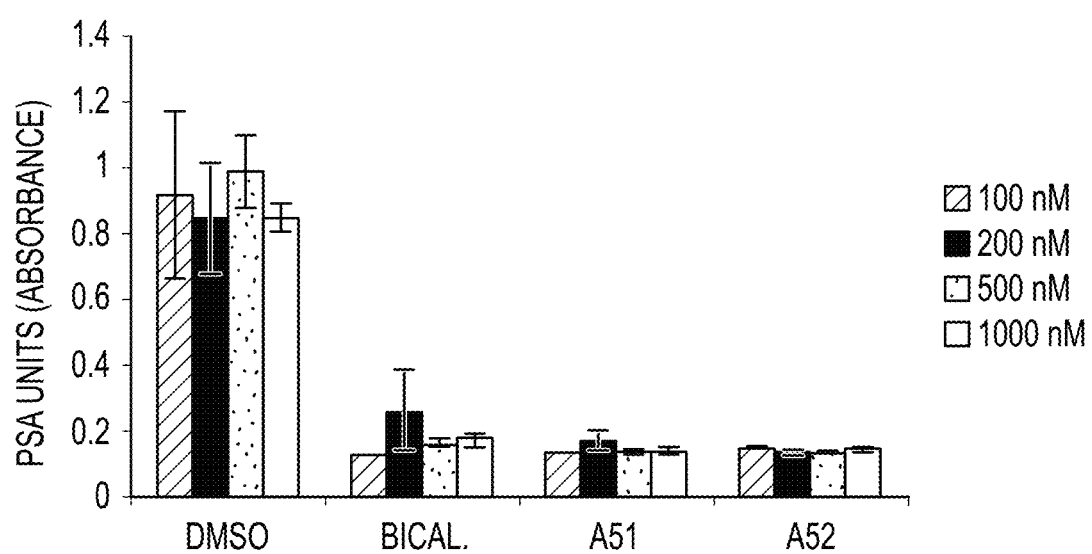
FIG. 1 is a bar chart depicting the antagonist effect of compounds A51 and A52 on HS cancer cells.

Embodiments of the invention are discussed in detail below. In describing embodiments, specific terminology is employed for the sake of clarity. However, the invention is not intended to be limited to the specific terminology so selected. A person skilled in the relevant art will recognize that other equivalent parts can be employed and other methods developed without parting from the spirit and scope of the invention. All references cited herein are incorporated by reference as if each had been individually incorporated.

The present invention relates to the compounds of formula II, methods of using such compounds as modulators of androgen receptors and to pharmaceutical compositions containing such compounds and salts thereof. Compounds of formula II can be used to agonize or antagonize the function of the nuclear receptor. The compounds can be used to antagonize the androgen receptor. Use of the compounds is not limited to affecting the androgen receptor, but can, for example, also be useful for the treatment of other diseases related to nuclear receptor function. Formula II can be represented as the structure Formula II

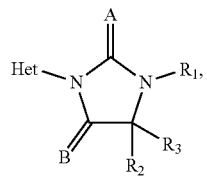

wherein, Het is a heterocyclic unit of 5 and 6 atoms. Preferred heterocyclic units are selected from compounds represented by the structures

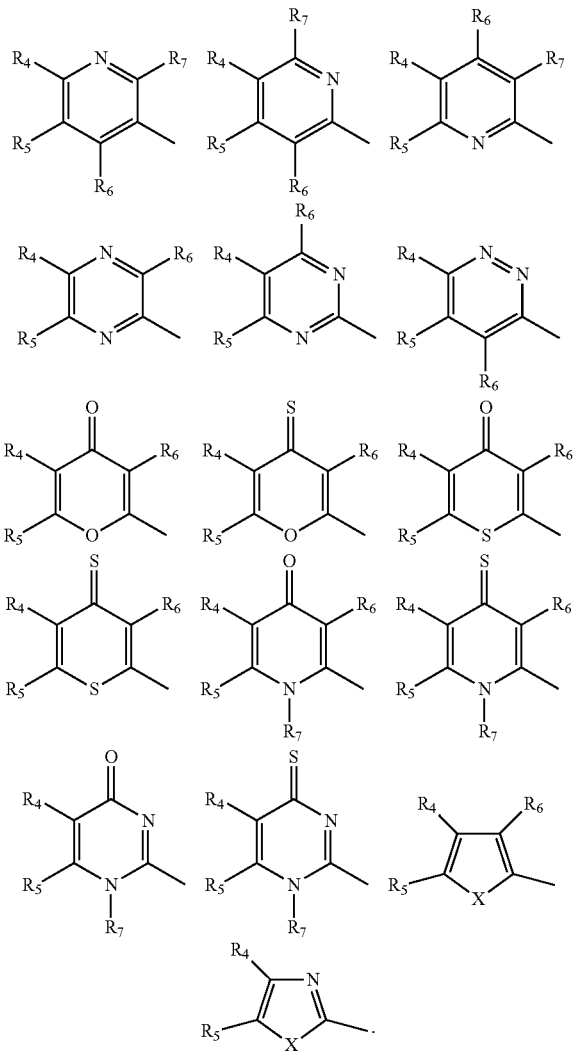

and the like. However, the invention is not intended to be limited to compounds having these structures.

Herein, $R_4$, $R_5$, $R_6$, and $R_7$ are independently selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, CN, $NO_2$, $OR_{11}$, $SR_{11}$, $NR_{11}R_{12}$, $NH(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$. $R_4$ is preferably CN or $NO_2$. $R_5$ is preferably trifluoromethyl, halogenated alkyl, halogenated alkenyl, halogenated alkynyl and halogen. $R_6$ and $R_7$ are preferably hydrogen, alkyl or halogen. $R_4$, $R_5$, $R_6$, and $R_7$ can be independently connected to form a cycle which can be aromatic, substituted aromatic, heterocyclic aromatic or non-aromatic, substituted heterocyclic aromatic or non-aromatic, cycloalkyl, substituted cycloalkyl. X is selected from sulfur (S), oxygen (O), $NR_8$ wherein N is nitrogen and $R_8$ is selected from the group consisting of hydrogen, alkyl, substituted alkyl, alkenyl, substituted alkenyl, alkynyl, substituted alkynyl, aryl, substituted aryl, arylalkyl, arylalkenyl, arylalkynyl, halogenated alkyl, halogenated alkenyl, halogenated alkynyl, halogen, $(CO)R_{11}$, $(CO)OR_{11}$, $(CS)R_{11}$, $(CS)OR_{11}$.

$R_1$ is selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$. $R_1$ is preferably aryl, substituted aryl, alkyl, substituted alkyl, alkenyl, substituted alkenyl.

$R_2$ and $R_3$ are independently selected from hydrogen, aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl. $R_2$ and $R_3$ can be connected to form a cycle which can be heterocyclic aromatic or non aromatic, substituted heterocyclic aromatic or non aromatic, cycloalkyl, substituted cycloalkyl. $R_1$ and $R_2$ can be connected to form a cycle which can be heterocyclic aromatic or non aromatic, substituted heterocyclic aromatic or non aromatic.

A and B are independently selected from oxygen (O), sulfur (S) and N—$R_9$. $R_9$ is selected from hydrogen, aryl, substituted aryl, alkyl, substituted alkyl, alkenyl, substituted alkenyl, alkynyl, substituted alkynyl, halogenated alkyl, halogenated alkenyl, halogenated alkynyl, arylalkyl, arylalkenyl, arylalkynyl, heterocyclic aromatic or non-aromatic, substituted heterocyclic aromatic or non-aromatic, cycloalkyl, substituted cycloalkyl, $SO_2R_{11}$, $NR_{11}R_{12}$, $NR_{12}(CO)OR_{11}$, $NH(CO)NR_{11}R_{12}$, $NR_{12}(CO)R_{11}$, $O(CO)R_{11}$, $O(CO)OR_{11}$, $O(CS)R_{11}$, $NR_{12}(CS)R_{11}$, $NH(CS)NR_{11}R_{12}$, $NR_{12}(CS)OR_{11}$.

$R_{11}$ and $R_{12}$, are independently selected from hydrogen, alkyl, substituted alkyl, alkenyl or substituted alkenyl, alkynyl or substituted alkynyl, aryl, substituted aryl, arylalkyl, arylalkenyl, arylalkynyl, heterocyclic aromatic or non-aromatic, substituted heterocyclic aromatic or non-aromatic. $R_{11}$ and $R_{12}$ can be connected to form a cycle which can be heterocyclic aromatic or non-aromatic, substituted heterocyclic aromatic, cycloalkyl, substituted cycloalkyl.

The following definitions apply to the terms as used throughout this specification, unless otherwise limited in specific instances.

As used herein, the term "alkyl" denotes branched or unbranched hydrocarbon chains, preferably having about 1 to about 8 carbons, such as, methyl, ethyl, n-propyl, isopropyl, n-butyl, sec-butyl, isobutyl, tert-butyl, 2-methylpentyl, pentyl, hexyl, isohexyl, heptyl, 4,4-dimethylpentyl, octyl, 2,2,4-trimethylpentyl and the like. "Substituted alkyl" includes an alkyl group optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocycloalkyl, bicycloalkyl and tricycloalkyl, containing a total of 3 to 20 carbons forming the rings, preferably 3 to 10 carbons, and which can be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloallcyl, alkylamido, alkanoylamino, oxo, acyl, arylcarbonylamino, amino, nitro, cyano, thiol and/or alkylthio and/or any of the substituents included in the definition of "substituted alkyl." For example,

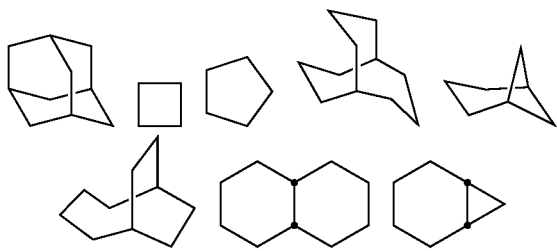

and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 1- and 2-phenylethyl, 2- and 3-phenylpropyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

The terms "halogenated alkyl", "halogenated alkenyl" and "halogenated alkynyl" as used herein alone or as part of another group refers to "alkyl", "alkenyl" and "alkynyl" which are substituted by one or more atoms selected from fluorine, chlorine, bromine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and can optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, alkyl, haloalkyl, alkoxy, haloalkoxy, alkenyl, trifluoromethyl, trifluoromethoxy, alkynyl, cycloalkyl, cycloalkylalkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), carbamoyl, alkyl carbamoyl, amidified carboxy, amidified carboxyalkyl, alkyl amidified carboxyalkyl, thiol, alkylthio, arylthio, heteroarylthio, arylthioalkyl, alkoxyarylthio, allcylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heterocyclic" or "heterocycle", as used herein, represents an unsubstituted or substituted stable 5- to 10-membered monocyclic ring system which can be saturated or unsaturated, and which consists of carbon atoms and from one to four heteroatoms selected from N, O, or S, and wherein the nitrogen and sulfur heteroatoms can optionally be oxidized; and the nitrogen heteroatom can optionally be quaternized. The heterocyclic ring can be attached at any heteroatom or carbon atom which results in the creation of a stable structure. Examples of such heterocyclic groups include, but are not limited to, piperidinyl, piperazinyl, oxopiperazinyl, oxopiperidinyl, oxopyrrolidinyl, azepinyl, oxoazepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g., benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

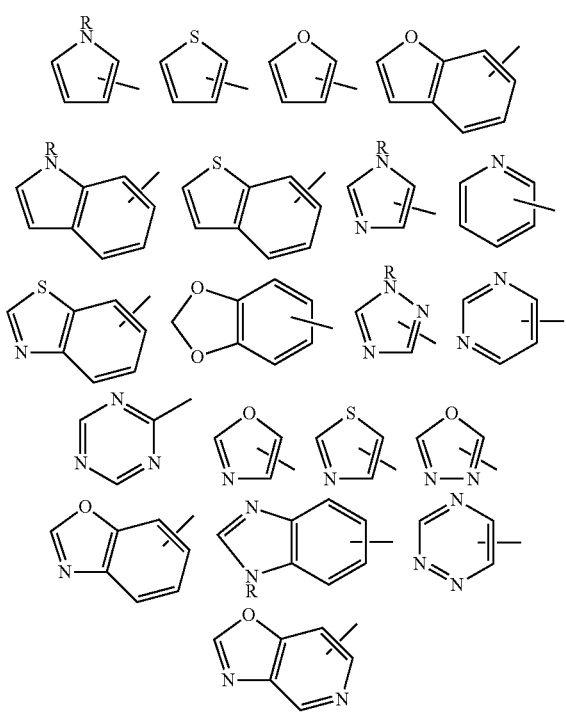

and the like.

The compounds of formula II can be present as salts, which are also within the scope of this invention. Pharmaceutically acceptable (i.e., non-toxic, physiologically acceptable) salts are preferred. If the compounds of formula II have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-C4) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula II having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts can furthermore be formed. Salts which are unsuitable for pharmaceutical uses but which can be employed, for example, for the isolation or purification of free compounds of formula II or their pharmaceutically acceptable salts, are also included. Preferred salts of the compounds of formula II which contain a basic group include monohydrochloride, hydrogensulfate, methanesulfonate, phosphate or nitrate. Preferred salts of the compounds of formula II which contain an acid group include sodium, potassium and magnesium salts and pharmaceutically acceptable organic amines.

The term "modulator" used in this invention refers to a chemical compound with capacity to either enhance (e.g., "agonist" activity) or inhibit (e.g., "antagonist" activity) a functional property of biological activity or process (e.g., enzyme activity or receptor binding); such enhancement or inhibition can be contingent on the occurrence of a specific event, such as activation of a signal transduction pathway, and/or can be manifest only in particular cell types.

The term "prodrug esters" as employed herein includes imines, esters and carbonates formed by reacting one or more hydroxyls of compounds of formula II with alkyl, alkoxy, or aryl substituted acylating agents employing procedures known to those skilled in the art to generate acetates, pivalates, methylcarbonates, benzoates and the like. Any compound that can be converted in vivo to provide the bioactive agent (i.e., the compound of formula II) is a prodrug within the scope and spirit of the invention. Various forms of prodrugs are well known in the art. A comprehensive description of prodrugs and prodrug derivatives are described in: (1) The Practice of Medicinal Chemistry, Camille G. Wermuth et al., Ch 31, (Academic Press, 1996); (2) Design of Prodrugs, edited by H. Bundgaard, (Elsevier, 1985); (3) A Textbook of Drug Design and Development, P. Krogsgaard-Larson and H. Bundgaard, eds. Ch 5, pgs 113-191 (Harwood Academic Publishers, 1991).

Synthesis

The compounds of formula II of the invention can be prepared as shown in the following reaction schemes and description thereof, as well as relevant published literature procedures that can be used by one skilled in the art. Exemplary reagents and procedures for these reactions appear hereinafter and in the working Examples.

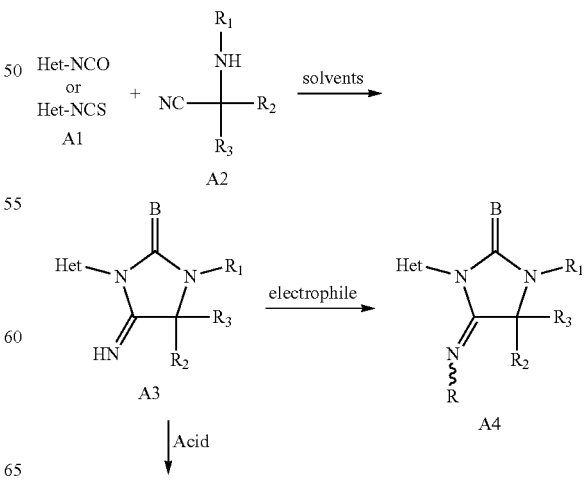

Scheme 1

-continued

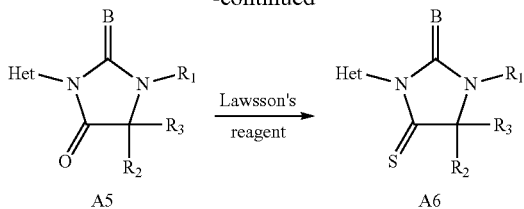

As illustrated in Scheme 1, compounds of formula A4 can be prepared from intermediate A3 with an appropriate electrophile. Intermediates of formula A3 can be obtained by reacting intermediates A1 with A2 in an appropriate solvent such as N,N-dimethylformamide. Intermediates A1 and A2 can be obtained commercially, can be prepared by methods known in the literature, or can be readily prepared by one skilled in the art. Compounds of formula A3 can be treated with acid to afford compounds of formula A5. Compounds of formula A5 can be treated with Lawesson's reagent to obtain compounds of formula A6.

Scheme 2: Synthesis of A51

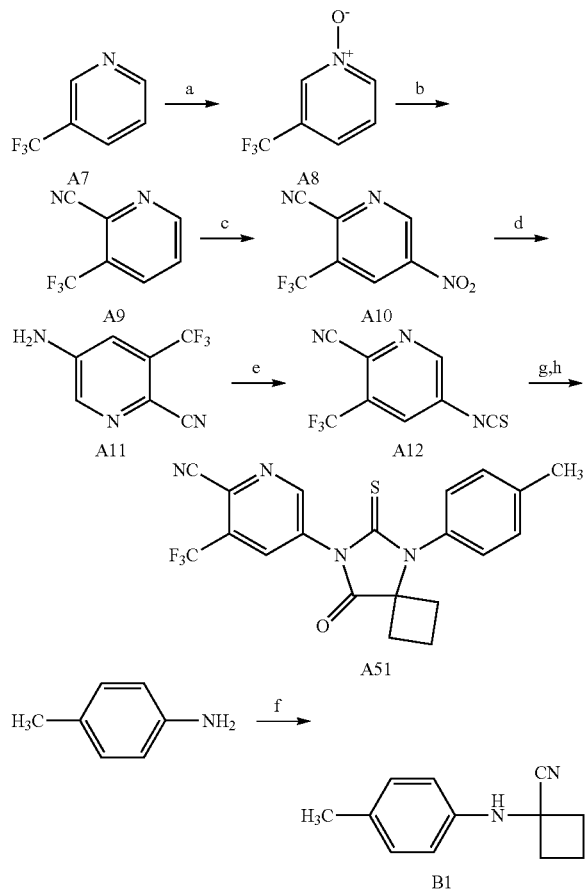

Synthesis of 3-(trifluoromethyl)pyridine-N-oxide, A8

To a mixture of 3-(trifluoromethyl)pyridine A7 (1.47 g, 10 mmol) and methyltrioxorhenium (0.0025 g, 0.01 mmol) in dichloromethane (2 ml) was added 30% hydrogen peroxide (4 ml). The mixture was stirred at room temperature for 5 hours. A small portion of $MnO_2$ (3 mg) was added and the medium was stirred for an additional 1 hour and then dichloromethane was added (50 ml). The medium was washed with brine, dried over $MgSO_4$ and concentrated to obtain compound A8 as an off-white powder (1.56 g, 9.6 mmol, 96%). $^1$H NMR (400 MHz, $CDCl_3$) δ 7.22-7.23 (m, 2H), 8.15 (d, J=3.6, 1H), 8.23 (s, 1H); $^{13}$C NMR (100 MHz, $CDCl_3$) δ 120.50 (q, J=3.5 Hz), 121.58 (q, J=271.4 Hz), 126.48, 130.10 (q, J=34.5 Hz), 136.52 (q, J=3.7 Hz), 141.89.

Synthesis of 2-cyano-3-(trifluoromethyl)pyridine. A9

To a solution of 3-(trifluoromethyl)pyridine-N-oxide A8 (1.3 g, 8 mmol) in acetonitrile was added trimethylsilyl cyanide (0.99 g, 10 mmol) and triethylamine (2.02 g, 20 mmol). The mixture was stirred at room temperature for 24 hours and then was washed with saturated $Na_2CO_3$ and extracted with dichloromethane. The organic layer was dried over $MgSO_4$ and concentrated to yield a brown residue which was chromatographed (EtOAc:Pentane, 1:2). Compound A9 was obtained as a light yellow solid (0.715 g, 4.16 mmol, 52%). $^1$H NMR (400 MHz, $CDCl_3$) δ 7.73 (dd, $J_1$=8.0 Hz, $J_2$=4.8 Hz, 1H), 8.15 (d, J=8.0 Hz, 1H), 8.91 (d, J=4.8 Hz, 1H); $^{13}$C NMR (100 MHz, $CDCl_3$) δ114.18, 121.74 (q, J=272.3 Hz), 126.65, 130.45 (q, J=33.8 Hz), 131.25, 134.66 (q, J=4.2 Hz), 153.44.

Synthesis of 2-cyano-3-(trifluoromethyl)-5-nitropyridine, A10

To a mixture of A9 (0.688 g, 4 mmol) and tetramethyl-ammonium nitrate (1.09 g, 8 mmol) in 1,2-dichloroethane was added trifluoroacetic anhydride (1.68 g, 8 mmol). The mixture was sealed and heated to 60° C. for 48 hours. The mixture was washed with saturated sodium bicarbonate and extracted with ethyl acetate. The organic layer was dried over $MgSO_4$ and concentrated to yield a yellow residue which was chromatographed (EtOAc:pentane, 1:4) to yield compound A10 (0.095 g, 0.44 mmol, 11%) and the remaining starting material. $^1$H NMR (400 MHz, $CDCl_3$) δ 8.91 (d, J=2.4 Hz, 1H), 9.69 (d, J=2.4 Hz, 1H); 9.69 (d, J=2.4 Hz, 1H); $^{13}$C NMR (100 MHz, $CDCl_3$) δ 112.70, 120.65 (q, J=273.5 Hz), 129.11, 130.40 (q, J=4.4 Hz), 131.58 (q, J=35.5 Hz), 144.22, 148.23.

Synthesis of 2-cyano-3-(trifluoromethyl)-5-aminopyridine, A11

A mixture of 2-cyano-3-(trifluoromethyl)-5-nitropyridine A10 (0.095 g, 0.44 mmol) and iron powder (0.112 g, 2 mmol) in ethyl acetate (1 ml) and acetic acid (1 ml) was heated for 15 hours. The solid particle was filtered through Celite and the filtrate was concentrated and chromatographed (EtOAc:pentane, 1:1) to yield compound A11 (0.075 g, 0.4 mmol, 91%). $^1$H NMR (400 MHz, $CDCl_3$) δ 6.36 (bs, 2H), 7.38 (d, J=2.4 Hz, 1H), 8.26 (d, J=2.4 Hz, 1H).
Alternatively, 2-cyano-3-(trifluoromethyl)-5-nitropyridine A10 can be reacted with hydrogen over Raney-Ni to obtain 2-cyano-3-(trifluoromethyl)-5-aminopyridine, A11.

Synthesis of 5-isothiocyanato-3-trifluoromethylpyridine-2-carbonitrile, A12

To a heterogeneous mixture of 2-cyano-3-(trifluoromethyl)-5-nitropyridine A11 (0.075 g, 0.4 mmol) in water (2 ml) was added thiophosgene (50 μl). The mixture was stirred for 2 hours and then washed with water and extracted with chloroform. The organic layer was dried over MgSO4 and concentrated to yield compound A12 (0.087 g, 0.38 mmol, 95%). ¹H NMR (400 MHz, CDCl₃) δ 7.85 (d, J=2.4 Hz, 1H), 8.72 (d, J=2.4 Hz, 1H); ¹³C NMR (100 MHz, CDCl₃) δ 113.61, 121.04 (q, J=273.1 Hz), 127.41, 130.38 (q, J=4.3 Hz), 131.44 (q, J=34.4 Hz), 133.55, 144.75, 150.30.

Synthesis of 1-(4-methylphenyl)aminocyclobutanenitrile, B1

Trimethylsilyl cyanide (0.93 ml, 7 mmol) was added dropwise to a mixture of p-toluidine (0.535 g, 5 mmol) and cyclobutanone (0.42 g, 6 mmol). The reaction mixture was stirred at room temperature for 6 h and then concentrated under vacuum to obtain a brown liquid which was subjected to chromatography (dichloromethane) to yield B1 (0.912 g, 4.9 mmol, 98%) as a yellowish solid.

Synthesis of 5-(8-oxo-6-thioxo-5-(4-methylphenyl)-5,7-diazaspiro[3.4]oct-7yl)-3-trifluoromethylpyridine-2-carbonitrile, A51

A mixture of A12 (0.057 g, 0.265 mmol) and B1 (0.05 g, 0.265 mmol) in DMF (0.5 ml) was stirred at room temperature for 24 h. To this mixture were added methanol (2 ml) and aq. 2N HCl (1 ml). The second mixture was refluxed for 2 h. After being cooled to room temperature, the reaction mixture was poured into cold water (10 ml) and extracted with ethyl acetate (20 ml). The organic layer was dried over MgSO4, concentrated and chromatographed (dichloromethane) to yield compound A51 (0.066 g, 0.159 mmol, 60%) as a white powder.

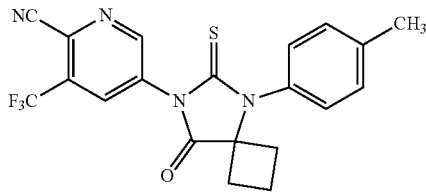 [SMILES: Cc1ccc(N2C(=S)N(c3cnc(C#N)c(C(F)(F)F)c3)C(=O)C23CCC3)cc1]

¹H NMR (CDCl₃, 400 MHz) δ 1.63-1.73 (m, 1H), 2.17-2.28 (m, 1H), 2.47 (s, 3H), 2.55-2.71 (m, 4H), 7.21 (d, J=8.4 Hz, 2H), 7.41 (d, J=8.4 Hz, 2H), 8.39 (d, J=2.0 Hz, 1H), 9.11 (d, J=2.0 Hz, 1H); ¹³C NMR (100 MHz, CDCl₃) δ 13.70, 21.38, 31.46, 67.61, 113.88, 121.36 (q, J=272.9 Hz), 129.45, 129.73, 130.40 (q, J=34.3 Hz), 130.86, 132.14, 132.53, 134.04 (q, J=4.3 Hz), 140.33, 152.37, 174.74, 179.17.

N-methyl-4-(1-cyanocyclobutylamino)-2-fluorobenzamide, B2

Sodium cyanide (1.47 g, 30 mmol) was added to a mixture of N-methyl 4-amino-2-fluorobenzamide (1.68 g, 10 mmol) and cyclobutanone (1.4 g, 20 mmol) in 90% acetic acid (20 ml). The reaction mixture was stirred at 80° C. for 24 hours. The mixture was washed with water and extracted with ethyl acetate. The organic layer was dried over magnesium sulfate and concentrated to dryness under vacuum. The solid was washed with a 50:50 mixture of ethyl ether and hexane (10 ml) to remove cyclobutanone cyanohydrin to afford after filtration B2 (2.19 g, 8.87 mmol, 89%). ¹H NMR (CDCl₃, 400 MHz) δ 1.87-1.95 (m, 1H), 2.16-2.27 (m, 1H), 2.35-2.41 (m, 2H), 2.76-2.83 (m, 2H), 2.97 (d, J=4.4 Hz, 3H), 4.68 (bs, 1H), 6.29 (dd, J=14.3, 1.8 Hz, 1H), 6.48 (dd, J=8.3, 1.8 Hz, 1H), 6.75 (q, J=4.4 Hz, 1H), 7.90 (dd, J=8.3, 8.3 Hz, 1H); ¹³C NMR (CDCl₃, 100 MHz) δ 15.7, 26.7, 33.9, 49.4, 100.2 (d, J=29.5 Hz), 110.6, 111.0 (d, J=11.8 Hz), 133.1 (d, J=4.2 Hz), 148.4 (d, J=12.0 Hz), 162.0 (d, J=244.1 Hz), 164.4 (d, J=3.6 Hz).

Synthesis of 4-[7-(6-cyano-5-trifluoromethylpyridin-3-yl)-8-oxo-6-thioxo-5,7-diazaspiro[3,4]oct-5-yl]-2-fluoro-N-methylbenzamide, A52

A mixture of A12 (0.03 g, 0.13 mmol) and B2 (0.032 g, 0.13 mmol) in DMF (0.5 ml) was heated under microwave irradiation at 80° C. for 20 hours. To this mixture was added methanol (2 ml) and aq. 2N HCl (1 ml). The second mixture was refluxed for 2 hours. After being cooled to room temperature, the reaction mixture was poured into cold water (10 ml) and extracted with ethyl acetate (15 ml). The organic layer was dried over MgSO4, concentrated and chromatographed (dichloromethane:acetone, 95:5) to yield A52 (0.022 g, 0.046 mmol, 35%) as a white powder.

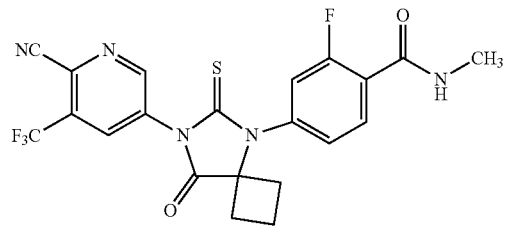 [SMILES: CNC(=O)c1ccc(N2C(=S)N(c3cnc(C#N)c(C(F)(F)F)c3)C(=O)C23CCC3)cc1F]

¹H NMR (CDCl₃, 400 MHz) δ 1.66-1.76 (m, 1H), 2.19-2.31 (m, 1H), 2.51-2.60 (m, 2H), 2.67-2.75 (m, 2H), 3.07 (d, J=4.9 Hz, 3H), 6.75 (q, J=4.8 Hz, 1H), 7.17 (dd, J=11.4, 1.9 Hz, 1H), 7.26 (dd, J=8.3, 1.9 Hz, 1H), 8.31 (dd, J=8.3, 8.3 Hz, 1H), 8.34 (d, J=2.1 Hz, 1H), 9.08 (d, J=2.1 Hz, 1H); ¹³C NMR (CDCl₃, 100 MHz) δ 13.6, 27.0; 31.7, 67.6, 113.7, 118.1, 118.4, 121.4 (q, J=272.9 Hz), 126.5, 130.0, 130.5 (q, J=34.5 Hz), 132.2, 133.7, 134.0, (q, J=4.2 Hz), 138.7 (d, J=10.7 Hz), 152.2, 160.5 (d, J=249.4 Hz), 162.6, 174.1, 179.0; ¹⁹F NMR (CDCl₃, 100 MHz) δ −110.94, −62.57.

Scheme 3: Synthesis of A52

In other embodiments, the present invention is directed to the method of synthesizing A52 described below. In some embodiments, Examples 1-8 can be performed sequentially to synthesize A52. However, as one of skill in the art will appreciate, this invention is not limited to the steps in Examples 1-8 as equivalent steps to those below are also encompassed by the present invention. Persons skilled in the art will recognize additional compounds that can be prepared utilizing similar methodology.

Synthesis of 3-(trifluoromethyl)pyridin-2(1H)-one, 2

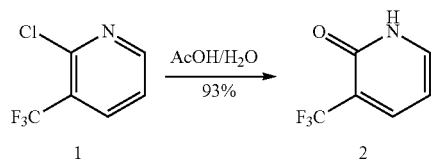 [SMILES: FC(F)(F)c1cccnc1Cl ; O=c1[nH]cccc1C(F)(F)F]

A solution of 2-chloro-3-(trifluoromethyl)pyridine 1 (5.00 g, 27.54 mmol) in a mixture of glacial acetic acid (50 ml) and water (5 ml) was refluxed for 7 days. The mixture was diluted with water (100 ml) and 6N aqueous NaOH was added until a pH of about 5 to about 6 was reached. The mixture was extracted with ethyl acetate (3×40 ml), the combined organic phases were dried over $Na_2SO_4$, and then all solvents were removed under reduced pressure. The resulting residue was dissolved in ethyl acetate and hexane was added to precipitate a product. After filtration, 3-(trifluoromethyl)pyridin-2(1H)-one 2 was obtained as an off-white powder (4.16 g, 25.51 mmol, 93%).

$^1$H NMR (400 MHz, DMSO) δ 12.31 (bs, 1H), 7.91 (d, J=7.1 Hz, 1H), 7.69 (d, J=6.4 Hz, 1H), 6.30 (t, J=6.7 Hz, 1H).[1]

Synthesis of
5-nitro-3-(trifluoromethyl)pyridin-2(1H)-one, 3

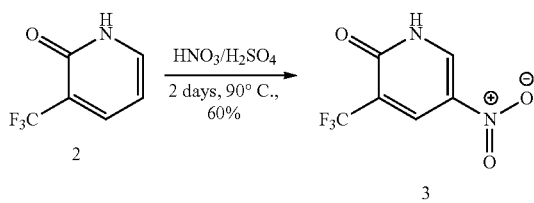 [SMILES: O=c1[nH]cccc1C(F)(F)F ; O=c1[nH]cc([N+](=O)[O-])cc1C(F)(F)F]

A mixture of 3-(trifluoromethyl)pyridin-2(1H)-one 2 (2.00 g, 12.26 mmol) and sulfuric acid ($H_2SO_4$, 3.5 ml, 30%) was heated to 90° C. and nitric acid ($HNO_3$, 2.5 ml, 65%) was added. The mixture was stirred at 90° C. for 8 hours and additional nitric acid (1 ml, 65%) was added. The mixture was stirred for an additional 6 hours at 90° C. and was then poured into a beaker containing ice (30 ml). The mixture was diluted with water (30 ml) and 6N aqueous NaOH was added until a pH of about 4 to about 5. The mixture was extracted with ethyl acetate (3×40 ml), the combined organic phases dried over $Na_2SO_4$ and all solvents were removed under reduced pressure. The residue was dissolved in ethyl acetate and the product precipitated by the addition of hexane. After filtration, 5-nitro-3-(trifluoromethyl)pyridin-2(1H)-one 3 was obtained as a yellow powder (1.58 g, 7.59 mmol, 62%).

$^1$H NMR (400 MHz, DMSO) δ 13.47 (bs, 1H), 8.95 (d, J=2.7 Hz, 1H), 8.46 (d, J=2.5 Hz, 1H).[2]

Synthesis of
2-chloro-5-nitro-3-(trifluoromethyl)pyridine, 4

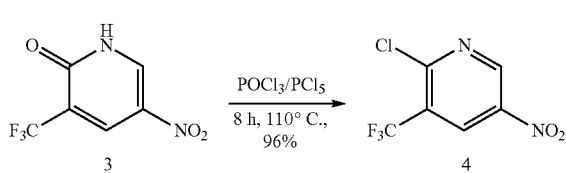 [SMILES: O=c1[nH]cc([N+](=O)[O-])cc1C(F)(F)F ; O=[N+]([O-])c1cnc(Cl)c(C(F)(F)F)c1]

A mixture of 5-nitro-3-(trifluoromethyl)pyridin-2(1H)-one 3 (1.50 g, 7.21 mmol), $POCl_3$ (2.76 g, 18.02 mmol) and $PCl_5$ (1.4 g, 10.09 mmol) is heated to about 110-120° C. for 8 hours and then poured into ice water. The mixture is neutralized with solid $NaHCO_3$ and extracted with ethyl acetate (3×40 ml). The combined organic phases is dried over $Na_2SO_4$ and all solvents removed under reduced pressure to obtain 2-chloro-5-nitro-3-(trifluoromethyl)pyridine 4.

Synthesis of
6-chloro-5-(trifluoromethyl)pyridin-3-amine. 5

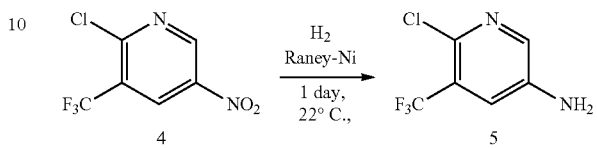

2-Chloro-5-nitro-3-(trifluoromethyl)pyridine 4 (1.57 g, 6.93 mmol) is dissolved in tetrahydrofuran (THF) (10 ml) and added to a suspension of Raney-Ni (200 mg) in THF (20 ml). Hydrogen gas is slowly bubbled through the stirred solution for 24 hours using a balloon. The mixture is filtered through Celite® (available from World Minerals, Inc., Lompoc, Calif.) and the solvent is removed under reduced pressure to obtain 6-chloro-5-(trifluoromethyl)pyridin-3-amine 5.

Synthesis of 1,1-dimethylethylcarbamate
N-6-chloro-5-(trifluoromethyl)pyridin-3-yl, 6

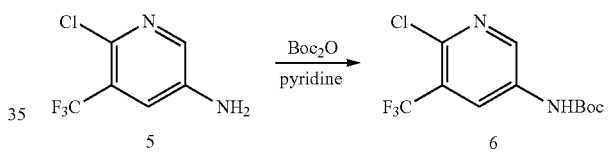

The crude 6-chloro-5-(trifluoromethyl)pyridin-3-amine 5 (1.3 g crude. 6.61 mmol) is dissolved in pyridine (10 ml) and 4-dimethylaminopyridine (DMAP) (50 mg) is added. Di-tert-butyl dicarbonate (2.17 g) is added dropwise and mixture stirred at 22° C. for 4 hours. Toluene (20 ml) is added and all solvents is removed under reduced pressure. The residue is filtered through a plug of silica gel (hexane/ethyl acetate 2:1) to obtain tert-butyl N-6-chloro-5-(trifluoromethyl)pyridin-3-ylcarbamate 6.

Synthesis of 5-amino-3-(trifluoromethyl)pyridine-2-carbonitrile, 8

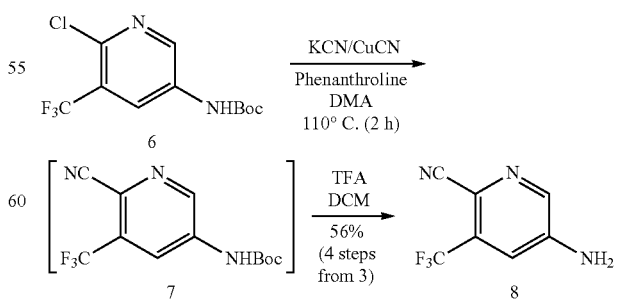

The crude tert-butyl N-6-chloro-5-(trifluoromethyl)pyridin-3-ylcarbamate 6 (2.4 g, 6.61 mmol) is dissolved in dimethylacetamide (DMA) (25 ml) and phenanthroline (120 mg, 0.66 mmol) is added. The mixture is heated to 80° C. and KCN (0.47 g, 7.27 mmol) is added. After stirring the mixture stirred for 10 min, CuCN (118 mg, 0.13 mmol) is added and the mixture stirred for 2 hours at 110° C. The cooled mixture is poured into a phosphate buffer (150 ml, pH 7), ethyl acetate (50 ml) is added and the mixture is filtered through Celite®. The layers are separated and the aqueous phase is extracted with ethyl acetate (3×40 ml). The combined organic phases are washed with saturated aqueous NaCl (4×30 ml), dried over $Na_2SO_4$ and all solvents removed under reduced pressure to produce the crude N-t-butoxycarbonyl nitrile 7.

The crude N-t-butoxycarbonyl nitrile 7 is dissolved in dichloromethane (20 ml) and trifluoroacetic acid (TFA) (4 ml is added. The mixture is stirred for 3 hours and evaporated. The residue is purified by column chromatography on silica gel (hexane/ethyl acetate 2:1) to obtain 5-amino-3-(trifluoromethyl)pyridine-2-carbonitrile 8.

Synthesis of 5-isothiocyanato-3-(trifluoromethyl)pyridine-2-carbonitrile, 9

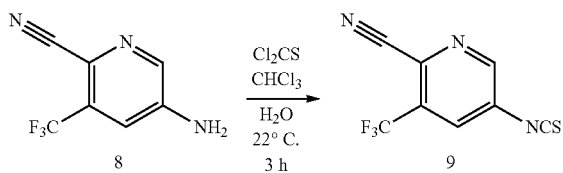

5-Amino-3-(trifluoromethyl)pyridine-2-carbonitrile 8 (1.141 g, 6.1 mmol) is mixed with chloroform (5 ml) and water (40 ml) to give a white suspension. Thiophosgene (0.701 ml, 9.15 mmol) is added and the reaction stirred for 2 hours at 22° C. to give a clear biphasic system. Chloroform (20 ml) is added and the phases are separated. The aqueous layer is extracted with chloroform (30 ml) and the combined organic is washed with saturated aqueous $NaHCO_3$ and water, dried over $MgSO_4$ and the solvent is removed under reduced pressure. The crude 5-isothiocyanato-3-(trifluoromethyl) pyridine-2-carbonitrile 9 is dried under vacuum and used as such in the next step, for example, in the step described in Example 8 below.

Synthesis of 4-(7-(6-cyano-5-(trifluoromethyl)pyridin-3-yl)-8-oxo-6-thioxo-5,7-diazaspiro[3.4]octan-5-yl)-2-fluoro-N-methylbenzamide 11, A52

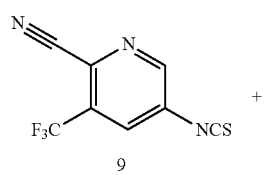

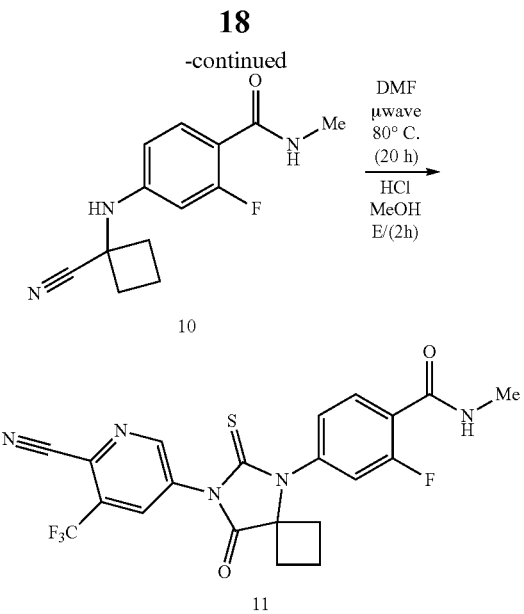

Crude 5-isothiocyanato-3-(trifluoromethyl)picolinonitrile 9 (1.390 g, 6.07 mmol) is placed in a 50 mL round-bottomed flask and 4-(1-cyanocyclobutylamino)-2-fluoro-N-methylbenzamide 10 (0.5 g, 2.022 mmol) is added to the flask. The mixture is left under vacuum (using an oil pump) for 1 hour. N,N-dimethylformamide (DMF) (6 ml) is added, the flask sealed under argon with a stopper and heated to 80° C. in a CEM microwave reactor for 20 hours. Methanol (10 ml) and 2N HCl (6 ml) is added and the mixture is refluxed for 2 hours. The mixture is diluted with water (30 ml) and saturated aqueous $NaHCO_3$ (30 ml) is added. The mixture is extracted with ethyl acetate (3×20 ml).

The combined organic layers is washed with saturated aqueous NaCl (20 ml), dried over $Na_2SO_4$, filtered and concentrated under reduced pressure. The crude product is purified by column chromatography on silica gel (dichloromethane/acetone 95:5) to obtain 4-(7-(6-cyano-5-(trifluoromethyl)pyridin-3-yl)-8-oxo-6-thioxo-5,7-diazaspiro[3.4]octan-5-yl)-2-fluoro-N-methylbenzamide 11.

Scheme 4: Synthesis of A52

EXAMPLE 1

Synthesis of 2-bromo-5-nitro-3-(trifluoromethyl)pyridine, 21

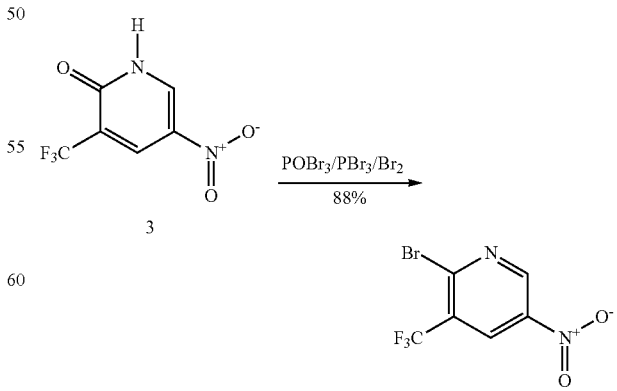

5-nitro-3-(trifluoromethyl)pyridin-2(1H)-one 3 is obtained by the routes provided in Examples 1 and 2 of Scheme 3, above.

A mixture of 5-nitro-3-(trifluoromethyl)pyridin-2(1H)-one 3, POBr$_3$ (1.5 equivalents), PBr$_3$ (4 equivalents), and Br$_2$ (2 equivalents) is heated to about 90-110° C. and is then poured into ice water. The mixture is neutralized and extracted. The combined organic phases are dried over Na$_2$SO$_4$ and all solvents removed under reduced pressure to obtain 2-bromo-5-nitro-3-(trifluoromethyl)pyridine 21 in a yield of 88%.

Alternatively, POBr$_3$ is substituted by POCl$_3$ to yield a mixture in the product having a ratio of bromine to chlorine substituents of 6:1 or better.

Synthesis of 5-nitro-3-(trifluoromethyl)pyridine-2-carbonitrile, 22

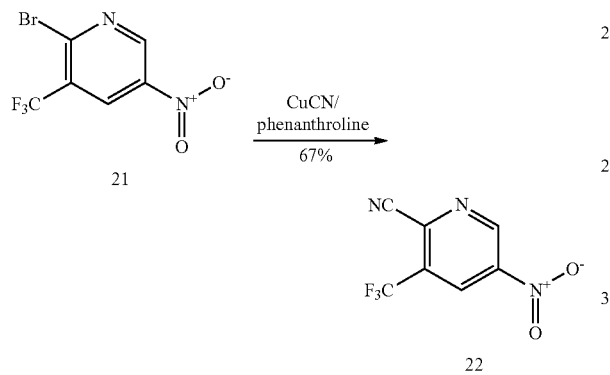

The crude 2-bromo-5-nitro-3-(trifluoromethyl)pyridine 21 is dissolved in dimethylacetamide (DMA) and phenanthroline (0.2 equivalents) is added. The mixture is heated to 160° C. and CuCN (2 equivalents) is added. The mixture is stirred for 40 minutes. Chromatography is performed to produce the 5-nitro-3-(trifluoromethyl)pyridine-2-carbonitrile 22 in a yield of 67%.

Synthesis of 5-amino-3-(trifluoromethyl)pyridine-2-carbonitrile, 8

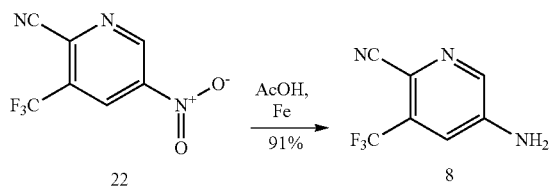 [SMILES: N#Cc1ncc([N+](=O)[O-])cc1C(F)(F)F ; N#Cc1ncc(N)cc1C(F)(F)F]

A mixture of 5-nitro-3-(trifluoromethyl)pyridine-2-carbonitrile 22 and iron powder in acetic acid is heated. 5-amino-3-(trifluoromethyl)pyridine-2-carbonitrile, 8 is obtained in a yield of 91%.

Synthesis of 4-(7-(6-cyano-5-(trifluoromethyl)pyridin-3-yl)-8-oxo-6-thioxo-5,7-diazaspiro[3.4]octan-5-yl)-2-fluoro-N-methylbenzamide 11, A52

5-amino-3-(trifluoromethyl)pyridine-2-carbonitrile 8 is treated as discussed in Example 7 of Scheme 3, above, to obtain 5-isothiocyanato-3-(trifluoromethyl)pyridine-2-carbonitrile 9.

5-isothiocyanato-3-(trifluoromethyl)pyridine-2-carbonitrile, 9 is reacted with 4-(1-cyanocyclobutylamino)-2-fluoro-N-methylbenzamide 10 as discussed in Example 8 of Scheme 3, above, to obtain 4-(7-(6-cyano-5-(trifluoromethyl)pyridin-3-yl)-8-oxo-6-thioxo-5,7-diazaspiro[3.4]octan-5-yl)-2-fluoro-N-methylbenzamide 11 (A52).

Scheme 5: Alternative Synthesis of A52

Synthesis of 3-(trifluoromethyl)-5-isothiocyanato-pyridine-2-carbonitrile (A)

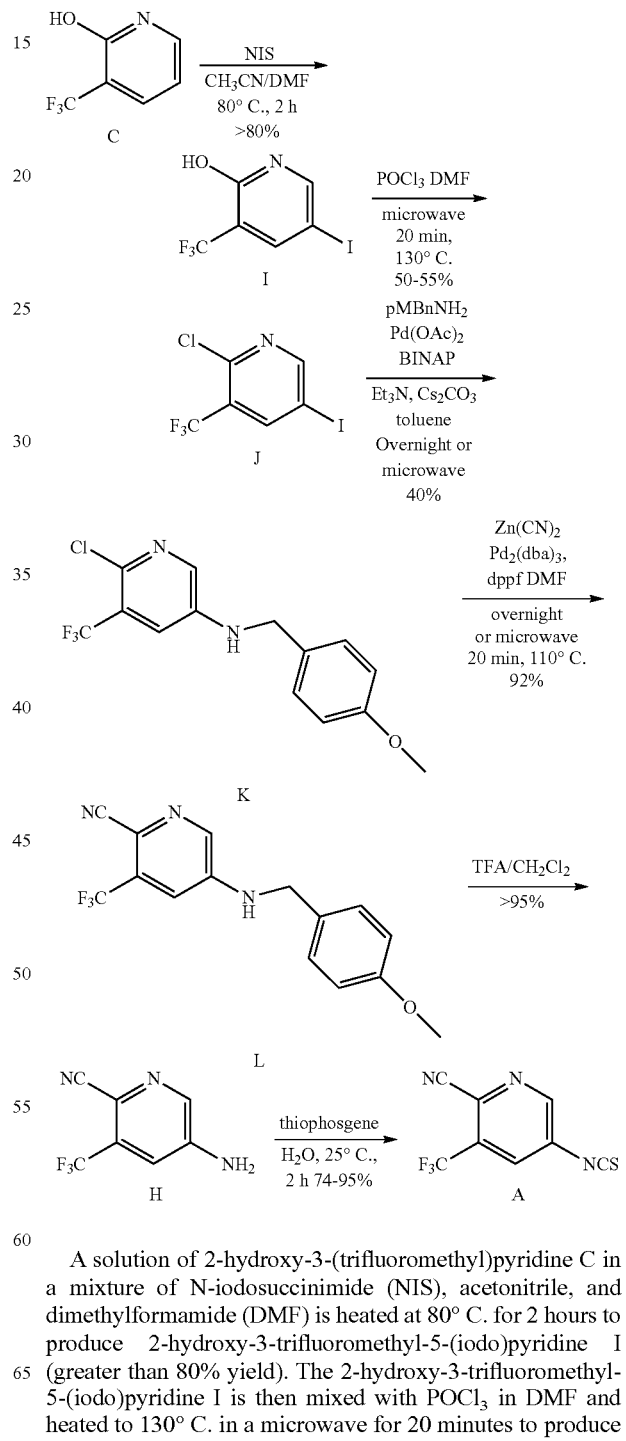

A solution of 2-hydroxy-3-(trifluoromethyl)pyridine C in a mixture of N-iodosuccinimide (NIS), acetonitrile, and dimethylformamide (DMF) is heated at 80° C. for 2 hours to produce 2-hydroxy-3-trifluoromethyl-5-(iodo)pyridine I (greater than 80% yield). The 2-hydroxy-3-trifluoromethyl-5-(iodo)pyridine I is then mixed with POCl$_3$ in DMF and heated to 130° C. in a microwave for 20 minutes to produce 2-chloro-3-trifluoromethyl-5-(iodo)pyridine J (yield of 50 to 55%). The 2-chloro-3-trifluoromethyl-5-(iodo)pyridine K is reacted in a solution of pMBnNH₂, palladium(II) acetate, 2,2'-bis(diphenylphosphino)-1,1'-binaphthyl (BINAP), triethylamine, and cesium carbonate in toluene to produce 5((4-methoxyphenyl))methylamino)-2-chloro-3-(trifluoromethyl)pyridine K (yield of 40%). The 5-((4-methoxyphenyl))methylamino)-2-chloro-3-(trifluoromethyl)pyridine K is reacted in a solution of zinc cyanide, tris(dibenzylideneacetone)dipalladium (Pd₂(dba)₃), and 1,1'-bis (diphenylphosphino)ferrocene (dppf) in DMF to provide 5-(4-methoxybenzylamine)-2-cyano-3-(trifluoromethyl)pyridine K (yield of 92%). The 5-(4-methoxybenzylamine)-2-cyano-3-(trifluoromethyl)pyridine K is reacted in a solution of dichloromethane and trifluoroacetic acid to provide 2-cyano-3-trifluoromethyl-5-(amino)pyridine H (yield greater than 95%). The 2-cyano-3-trifluoromethyl-5-(amino)pyridine H is reacted with thiophosgene in water at 25° C. for 2 hours to provide 5-isothiocyanato-3-(trifluoromethyl)pyridine-2-carbonitrile A (yield of 74% to 95%).

Synthesis of 4-(1-cyanocyclobutylamino)-2-fluoro-N-methylbenzamide intermediate B

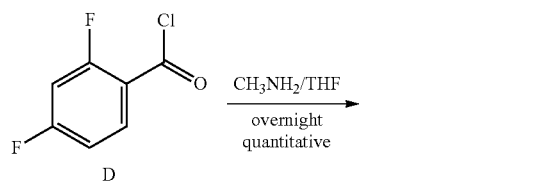

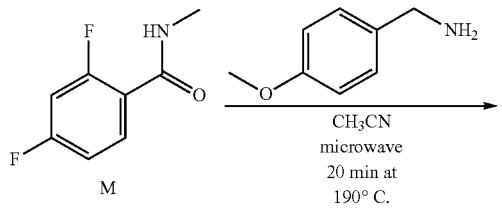

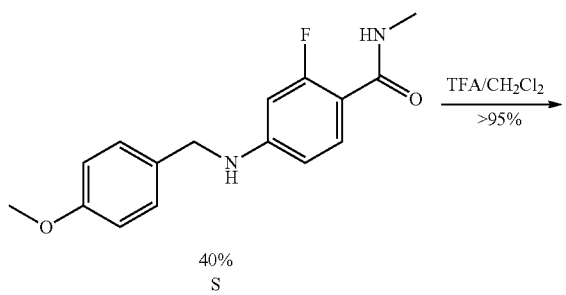

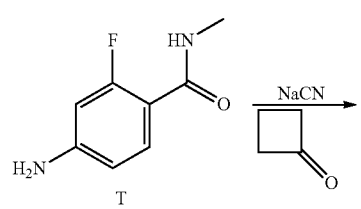

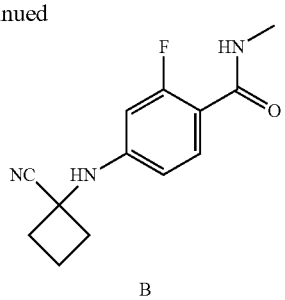

B

A solution of 2,4-difluoro-benzoylchloride D in a solution of methylamine and tetrahydrofuran (THF) is allowed to react to produce 2,4-difluoro-N-methylbenzamide M (quantitative yield). The 2,4-difluoro-N-methylbenzamide M is mixed with in a solution of acetonitrile and 4-methoxybenzenemethanamine and heated in a microwave for 20 minutes at 190° C. to produce 2-fluoro-4-(4-methoxybenzylamino)-N-methylbenzamide S (yield of 40%). The 2-fluoro-4-(4-methoxybenzylamino)-N-methylbenzamide S is reacted in a solution of dichloromethane and trifluoroacetic acid to produce 2-fluoro-4-amino-N-methylbenzamide T (yield greater than 95%). The 2-fluoro-4-amino-N-methylbenzamide T is reacted with a solution of sodium cyanide and cyclobutanone to produce 4-(1-cyanocyclobutylamino)-2-fluoro-N-methylbenzamide B.

Coupling of A and B to produce 4-(7-(6-cyano-5-(trifluoromethyl)pyridin-3-yl)-8-oxo-6-thioxo-5,7-diazaspiro[3,4]octan-5-yl)-2-fluoro-N-methylbenzamide, A52

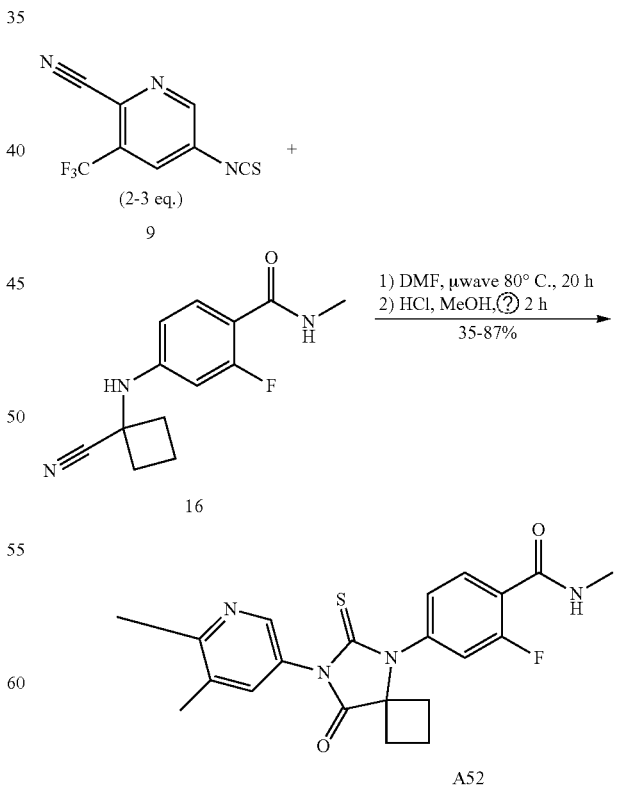

5-isothiocyanato-3-(trifluoromethyl)pyridine-2-carbonitrile, 9, A is reacted with 4-(1-cyanocyclobutylamino)-2- fluoro-N-methylbenzamide B in DMF solution by heating in a microwave at 80° C. for 20 hours. Methanol and hydrochloric acid are then added and the reaction allowed to proceed for 2 hours to produce 4-(7-(6-cyano-5-(trifluoromethyl)pyridin-3-yl)-8-oxo-6-thioxo-5,7-diazaspiro[3.4]octan-5-yl)-2-fluoro-N-methylbenzamide, A52 (yield 35 to 87%).

Activity

Utility

The compounds of the present invention modulate the function of the nuclear hormone receptors, particularly the androgen receptor, and include compounds which are, for example, selective agonists or selective antagonists of the androgen receptor (AR). Thus, the present compounds are useful in the treatment of AR-associated conditions. An "AR-associated condition," as used herein, denotes a condition or disorder which can be treated by modulating the function or activity of an AR in a subject, wherein treatment comprises prevention, partial alleviation or cure of the condition or disorder. Modulation can occur locally, for example, within certain tissues of the subject, or more extensively throughout a subject being treated for such a condition or disorder. Preferably, the compounds with potent antagonistic activity are used for the treatment of androgen related prostate cancer.

Combination

The present invention includes within its scope pharmaceutical compositions comprising, as an active ingredient, a therapeutically effective amount of at least one of the compounds of formula II, alone or in combination with a pharmaceutical carrier or diluent. Optionally, compounds of the present invention can be used alone, in combination with other compounds of the invention, or in combination with one or more other therapeutic agent(s), e.g., an antibiotic or other pharmaceutically active material.

Pharmacological Assay

The compounds in this invention were identified through screening on hormone sensitive and hormone refractory prostate cancer cells for antagonistic and agonistic activities. The compounds with antagonist activity are potential drugs for the treatment of prostate cancer, both hormone sensitive and hormone refractory.

Figure 2:
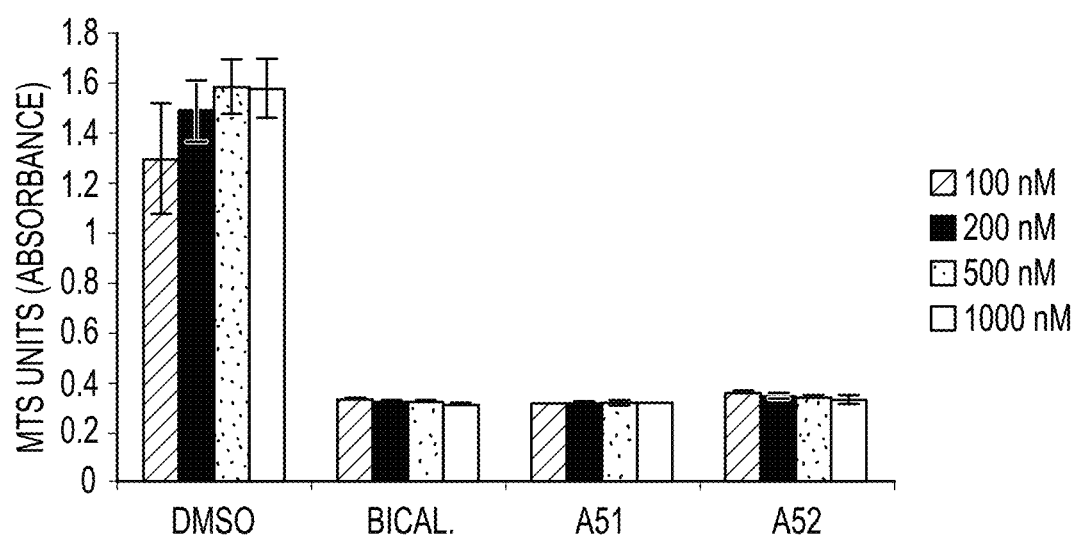
FIG. 2 is a bar chart depicting the antagonist effect of compounds A51 and A52 on HS cancer cells.
Figure 3:
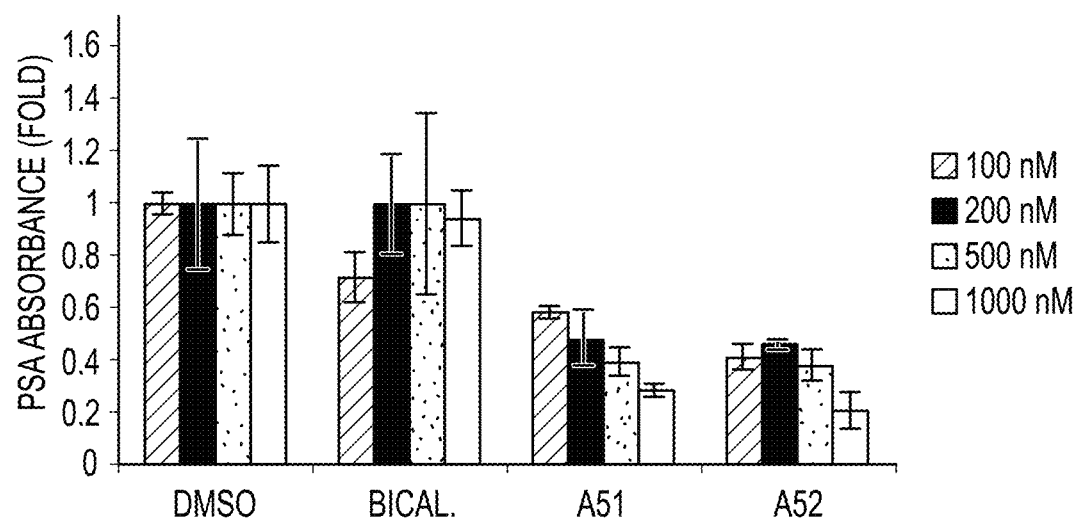
FIG. 3 is a bar chart depicting the antagonist effect of compounds A51 and A52 on HR cancer cells.

The biological activity of the compound of formula II was measured by secreted levels of prostate specific antigen (PSA). It is well established that PSA levels are indicators of AR activities in prostate cancer. To examine if the compounds affect AR function in a physiological environment, we determined secreted levels of endogenous PSA induced by R1881 in the hormone sensitive (HS) and hormone refractory (HR) cancer cells. HR cells are LNCaP cells engineered to express elevated levels of androgen receptor protein (LNCaP/AR cells), analogous to levels observed in patients with HR cancer who relapse while taking current antiandrogens such as bicalutamide, which acquire agonist properties when AR is highly expressed. LNCaP cells (or LNCaP/AR cells) were maintained in Iscove's medium containing 10% FBS. Five days prior to drug treatment, the cells were grown in Iscove's medium containing 10% CS-FBS to deprive of androgens. The cells were split and grown in Iscove's medium containing 10% CS-FBS with appropriate concentrations of R1881 and the test compounds. After 5 days of incubation, secreted PSA levels were assayed using PSA ELISA kits (American Qualex, San Clemente, Calif.) (See FIG. 1 and FIG. 3). The MTS assay was also used to examine the growth inhibition of the compounds of formula II (See FIG. 2).

Pharmacokinetic Data

Figure 4:
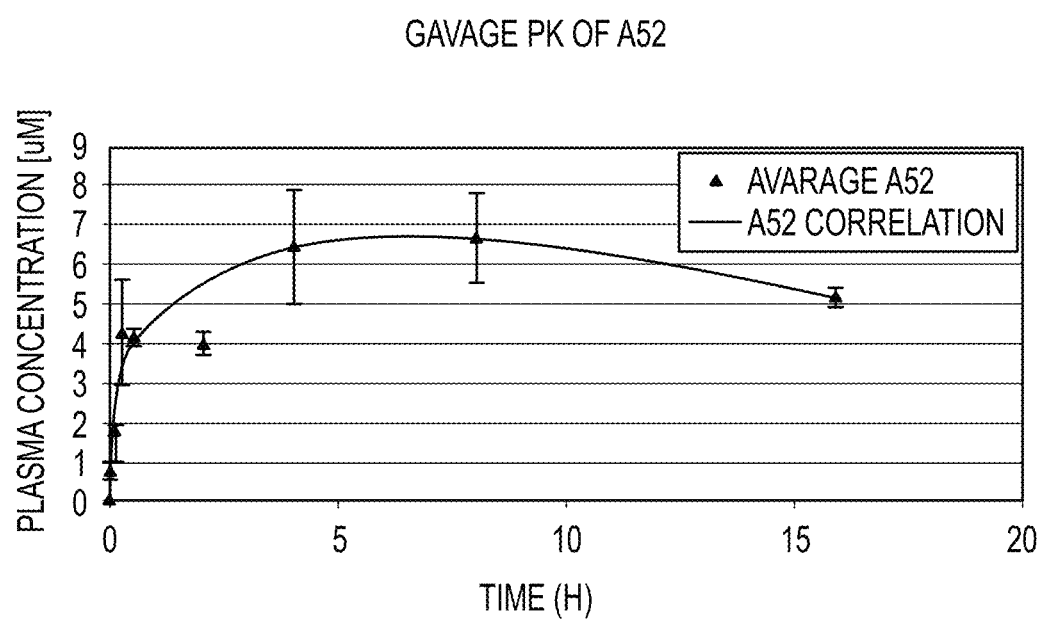
FIG. 4 is a graph depicting the pharmacokinetic behavior of compound A52.

The pharmacokinetics of A52 was evaluated in vivo using 8 week-old FVB mice which were purchased from Charles River Laboratories. Mice were divided into groups of three for each time point (See FIG. 4). Two mice were not treated with drug and two other mice were treated with vehicle solution. Each group was treated with 10 mg per kilogram of body weight. The drug was dissolved in a mixture 50:10:1:989 of DMSO:Carboxymethylcellulose:T Tween 80:$H_2O$ (Vehicle solution) and was administered orally. After drug administration, the animals were euthanized via $CO_2$ inhalation at different timepoints: 1 min, 5 min, 15 min, 30 min, 2 h, 4 h, 8 h, 16 h. Animals were immediately bleed after exposure to $CO_2$ via cardiac puncture (1 ml BD syringe+27G 5/8 needle).

The serum samples were analyzed to determine the drug's concentration by the HPLC which (Waters 600 pump, Waters 600 controller and Waters 2487 detector) was equipped with an Alltima C18 column (3µ, 150 mm×4.6 mm). All RD compounds were detected at 254 nm wave length and bicalutamide was detected at 270 nm wave length.

The samples for HPLC analysis were prepared according to the following procedure:

Blood cells were separated from serum by centrifugation. To 400 µl of serum were added 80 µl of a 10 µM solution of RD75 in acetonitrile as internal standard and 520 µl of acetonitrile. Precipitation occurred.

The mixture was vortexed for 3 minutes and then placed under ultrasound for 30 minutes.

The solid particles were filtered off or were separated by centrifugation.

The filtrate was dried under an argon flow to dryness. The sample was reconstructed to 80 µl with acetonitrile before analyzing by HPLC to determine the drug concentration.

Standard curve of drug was used to improve accuracy.

In Vivo Assay

Figure 5:
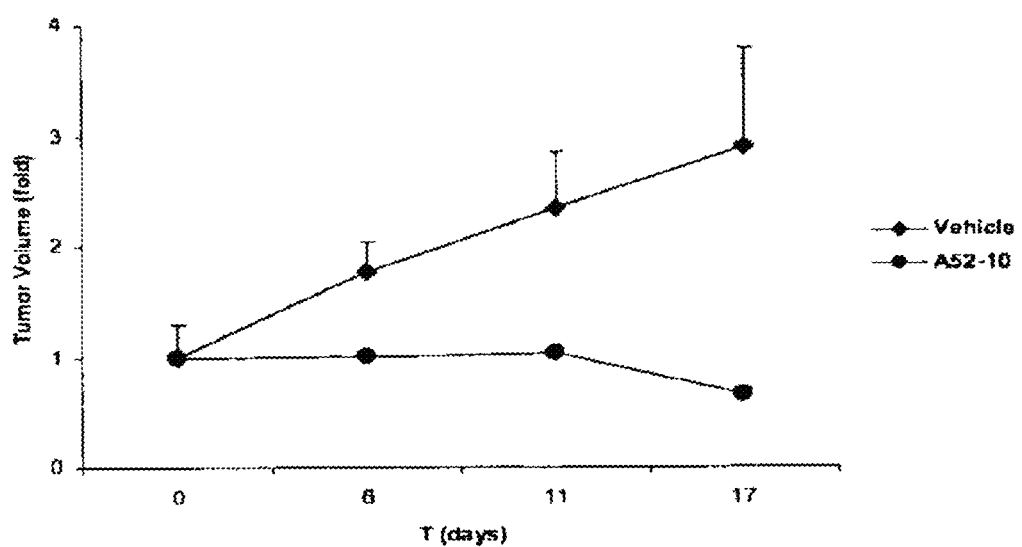
FIG. 5 is a graph depicting the effect of compound A52 on LnCaP-AR-overexpressed tumor size at 10 mg/kg.
Figure 6:
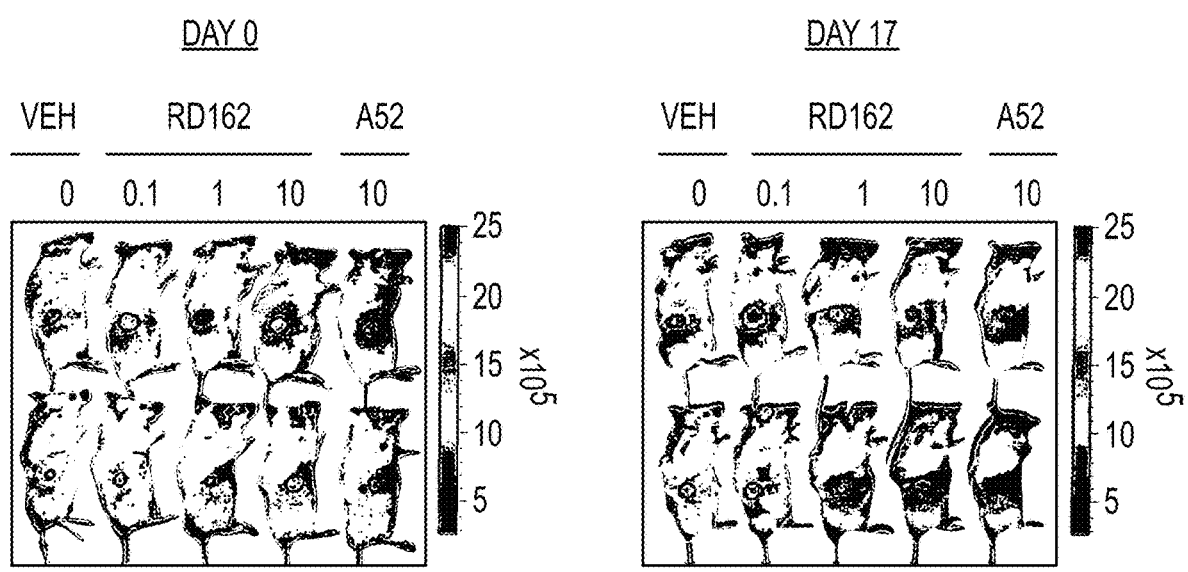
FIG. 6 presents images depicting the disappearance of Luciferase activity after 17 days of treatment with compound A52.

All animal experiments were performed in compliance with the guidelines of the Animal Research Committee of the University of California at Los Angeles. Animals were bought from Taconic and maintained in a laminar flow tower in a defined flora colony. LNCaP-AR and LNCaP-vector cells were maintained in RPMI medium supplemented with 10% FBS. $10^6$ cells in 100 µl of 1:1 Matrigel to RPMI medium were injected subcutaneously into the flanks of intact or castrated male SCID mice. Tumor size was measured weekly in three dimensions (length×width×depth) using calipers. Mice were randomized to treatment groups when tumor size reached approximately 100 $mm^3$. Drugs were given orally everyday at the dose of 10 mg/kg. (See FIG. 5 and FIG. 6) At a daily dose of 10 mg/kg, compounds A51 and A52 were found to completely retard tumor growth.

Other doses were also tried. At a daily dose of 1 mg/kg, compounds A51 and A52 were found to have a mild effect. At a daily dose of 25-50 mg/kg, compounds A51 and A52 were found induce some tumor cytotoxicity.

Prostate cancer cell lines were used for xenografts. For example, a LNCaP xenograft, LAPC4 xenograft, LAPC9 xenograft, and xenografts of the hormone refractory counterparts of these cell lines were made. Other cell lines included V-cap, CWR22 and LAPC4 cell lines. Two cell lines that over express the androgen receptor were generated, LNCaP AR and LAPC4 AR. Prostate cancer progression in these engineered cell lines was found to differ from their parental counterparts. Under androgen ablation, the LNCaP AR and LAPC4 AR lines continued to grow, thus behaving like hormone refractory cells.

Some of the cell lines were found to not take well in mice in tumor formation when xenografted. However, with LNCaP, 2 million cells gave a 95% take. As few as 1 million cells can be used. These cells required at least 25% Matrigel but no more than 50%. Since high concentrations of cells are required for good tumor take rate, a 27G needle was found to be the smallest appropriate needle.

The LAPC4 cell line was found to be very difficult to grow in animals. The cells need to be resuspended and filtered through a micron mesh filter, for example, a 40-100 micron mesh filter, because they frequently form large aggregates. Resuspending and running through a filter helps normalize the cell number between each animal and therefore gives more consistent results. LAPC4 requires from about 25%-50% Matrigel, for example, 50% Matrigel, but can be grafted successfully at a lower concentration at $10^5$ cells.

Tumor take in SCID mice was found to be better than in nude mice. For example, the tumor take across individual animal in nude mice was found to be very inconsistent. CB17 SCID mice were used in the study.

Injections were made subcutaneously on the right flank of the mouse. Slow injection was found to help to produce a round tumor that was easier to measure and could be measured more accurately. In addition, because of the usage of Matrigel, injection of no more than 200 µl was found appropriate. Injection of 100-200 µl was found appropriate. Injecting too large a volume created leakage upon needle withdrawal.

An alternative method to help prevent leakage from needle pullout can be to warm the Matrigel:media:cells filled syringe a couple of seconds to produce a gel-like form. When injecting the gel-like liquid, no leakage should occur. However, allowing the Matrigel to heat for too long a time can cause the suspension to solidify and become uninjectable.

Pharmaceutical Compositions and Administration

The compounds of the invention are useful as pharmaceutical compositions prepared with a therapeutically effective amount of a compound of the invention, as defined herein, and a pharmaceutically acceptable carrier or diluent.

The compounds of the invention can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue. Such compositions and preparations should contain at least 0.01% of a compound or compounds of the invention. The percentage of the compositions and preparations may, of course, be varied and may, for example, be between about 0.05% to about 2% of the weight of a given unit dosage form. The amount of compounds in such therapeutically useful compositions is such that an effective dosage level will be obtained.

Thus, compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with a fine inert powdered carrier and inhaled by the subject or insufflated. Such compositions and preparations should contain at least 0.1% of a compound or compounds of the invention. The percentage of the compositions and preparations may, of course, be varied and may conveniently be between about 2% to about 60% of the weight of a given unit dosage form. The amount of compounds in such therapeutically useful compositions is such that an effective dosage level will be obtained.

The tablets, troches, pills, capsules, and the like may also contain the following: binders such as gum tragacanth, *acacia*, corn starch, or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain the active compound, sucrose or fructose as a sweetening agent, methyl and propylparabens as preservatives, a dye, and flavoring such as cherry or orange flavor. Of course, any material used in preparing any unit dosage form should be pharmaceutically acceptable and substantially non-toxic in the amounts employed. In addition, the compounds of the invention may be incorporated into sustained-release preparations and devices. For example, the compounds may be incorporated into time release capsules, time release tablets, and time release pills.

The compounds of the invention may also be administered intravenously or intraperitoneally by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds of the invention which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the compounds of the invention in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds of the invention may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Other solid carriers include noatoxic polymeric nanoparticles or microparticles. Useful liquid carriers include water, alcohols, or glycols or water/alcohol/glycol blends, in which the compounds of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508), all of which are hereby incorporated by reference.

Useful dosages of the compounds of Formula II can be determined by comparing their in vitro activity, and by comparing their in vivo activity in animal models. Methods for the extrapolation of effective dosages in mice and other animals to humans are known to the art; for example, see U.S. Pat. No. 4,938,949, which is hereby incorporated by reference.

For example, the concentration of the compounds in a liquid composition, such as a lotion, can be from about 0.1 to about 25% by weight, or from about 0.5 to about 10% by weight. The concentration in a semi-solid or solid composition such as a gel or a powder can be from about 0.1 to about 5% by weight, or from about 0.5 to about 2.5% by weight.

The amount of the compounds of the invention required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight, and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.01 to about 500 mg/kg per day, e.g., from about 0.1 to about 500 mg/kg of body weight per day, such as from about 0.1 to about 100 mg per kilogram body weight of the recipient per day. For example, a suitable dose may be about 1 mg/kg, 10 mg/kg, or 50 mg/kg of body weight per day.

The compounds of the invention are conveniently administered in unit dosage form; for example, containing from about 0.0005 to about 500 mg, from about 0.01 to about 50 mg, from about 0.05 to about 10 mg, or about 5 mg of active ingredient per unit dosage form.

The compounds of the invention can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. This may be achieved, for example, by the intravenous injection of a 0.05 to 5% solution of the compounds of the present invention, optionally in saline, or orally administered as a bolus containing about 1-1000 mg of the compounds. Desirable blood levels may be maintained by continuous infusion to provide from about 0.0005 to about 25 mg per kg body weight per hour, for example at least or no more than 0.0005, 0.005, 0.05, 0.5, 5, or 25 mg/kg/hr. Alternatively, such levels can be obtained by intermittent infusions containing from about 0.002 to about 100 mg per kg body weight, for example, at least or no more than 0.002, 0.02, 0.2, 2, 20, 50, or 100 mg of the compounds per kg of body weight.

The compounds of the invention may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

Example: Intravenous Formulation

A compound presently disclosed, for example, compound A51 or A52, can be in a formulation suitable for intravenous dosing. In an embodiment, the compound is dissolved in from about 10% to about 25% dimethylsulfoxide (DMSO). 1× phosphate buffered saline (PBS) is then mixed into the solution as the balance, and the solution is sonicated with a water bath sonicator until it is homogeneous.

At a compound concentration of 1.5 mg/mL, 5 minutes of sonication may be sufficient to dissolve the compound. At a compound concentration of 2 mg/ml, more than 5 minutes of sonication may be required to dissolve the compound and a polyethylene glcyol can be added to keep the compound in suspension. For example, 5 to 40% PEG-400 (a polyethylene glycol), such as, 5-10% PEG-400, can be added.

The above solution, including either A51 or A52, was found to be stable at room temperature for at least a week.

Before administration, the above solution should be sonicated for a few minutes. A maximum appropriate administration volume for mice was found to be 0.2 mL.

When administered to mice, hardening of the skin and skin irritation around the injection site was observed, and this was attributed to the use of DMSO. Although compounds A51 and A52 are soluble in ethanol, ethanol was found to reduce the stability of the compounds in vivo.

Over a period of 2 weeks following administration of the above solution, mice were observed to lose 15% of body weight.

Example: Oral Formulation

A compound presently disclosed, for example, compound A51 or A52, can be in a formulation suitable for oral administration. In an embodiment, the compound is dissolved in 100% DMSO.

Additional chemicals can be added, such as a carboxymethylcellulose, a polysorbate, or water. For example, the components of the solution other than A51 or A52 can be present at concentrations of from about 10% to about 20% DMSO, from about 1% to about 2% carboxymethylcellulose (CMC), and 0.1% Tween 80 (a polysorbate), with the balance being water. The concentration of compound A51 or A52 in the oral foundation can be about 1.5 mg/mL. The solution is mechanically homogenized for at least 30 seconds. The compound A51 or A52 was found to stay in suspension for only a couple of hours and, therefore, the oral formulation must be administered within a couple of hours of preparation.

When more than 2% carboxymethylcellulose (CMC) was included in the solution, the formulation was found to be very viscous, so that when administered to a test animal with a gavage syringe, much of the formulation was left behind on the walls of the syringe, preventing accurate drug administration. A solution of 10% DMSO that included CMC and Tween 80 was found to keep the compound in suspension when mechanical homogenization was applied. That is, more than 10% DMSO was not required. A minimum of DMSO should be used, because it was found to irritate the mice, and was associated with a loss of up to 10% of the bodyweight of the mice over a period of 2 weeks following administration.

A maximum appropriate administration volume for mice was found to be 0.2 mL.

The half life of the compound was found to be longer when it was administered intravenously than when it was administered orally. However, daily oral dosing resulted in an acceptable steady state serum concentration of the compound, comparable to the steady state concentration seen with bicalutamide. Oral administration may be more convenient than intravenous administration.

Compounds A51 and A52 have a beneficial effect on tumors in an in vivo assay administered as described.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for treating a patient with a hyperproliferative disorder, comprising administering to a patient in need thereof a pharmaceutical composition comprising a pharmaceutically acceptable carrier, diluent, or adjuvant and a compound of Formula II:

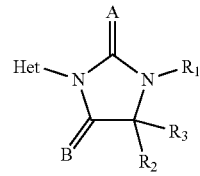

Formula II or a pharmaceutically acceptable salt thereof,
wherein:
A is S;
B is O;
Het is pyridyl, optionally substituted with 1, 2, 3, or 4 substituents independently selected from the group consisting of halogen, cyano, nitro, alkyl, alkenyl, alkynyl, $NR_{11}R_{12}$, $NR_{12}C(O)R_{11}$, $NHC(O)NR_{11}R_{12}$, $NHC(O)OR_{11}$, $NR_{12}C(S)R_{11}$, $NHC(S)NR_{11}R_{12}$, $NR_{12}C(S)OR^{11}$, $OR_{11}$, $OC(O)R_{11}$, $OC(O)OR_{11}$, $OC(S)R_{11}$, $SR_{11}$, and aryl;
$R_1$ is aryl;
$R_2$ and $R_3$, together with the carbon atom to which they are linked, form a $C_{3-10}$ cycloalkyl;
$R_{11}$ is hydrogen, alkyl, alkenyl, alkynyl, heterocyclic non-aromatic, aryl, or heterocyclic aromatic; and
$R_{12}$ is hydrogen, alkyl, alkenyl, alkynyl, heterocyclic non-aromatic, aryl, or heterocyclic aromatic;
wherein each alkyl is optionally substituted with 1 or more substituents independently selected from the group consisting of fluoro, chloro, bromo, iodo, cyano, nitro, alkyl, carbalkoyl, alkenyl, amido, carboxy, amino, hydroxy, alkoxy, thiol, alkylthio, heterocyclyl, aryl, and heteroaryl;
wherein each alkenyl, alkynyl, or substituted heterocyclic non-aromatic is optionally substituted with 1 or more substituents independently selected from the group consisting of halogen, cyano, nitro, oxo, alkyl, carbalkoyl, arylalkyl, alkenyl, acyl, amido, alkylamido, carboxy, amino, alkanoylamino, arylcarbonylamino, hydroxy, alkoxy, aryloxy, thiol, alkylthio, cycloalkyl, heterocyclyl, aryl, and heteroaryl;
wherein each aryl is optionally substituted with 1 or more substituents independently selected from the group consisting of halogen, cyano, nitro, alkyl, haloalkyl, carbalkoyl, amidified carboxyalkyl, alkyl amidified carboxyalkyl, aryloxyalkyl, arylthioalkyl, arylsulfinylalkyl, cycloalkylalkyl, cycloheteroalkylalkyl, arylalkyl, heteroarylalkyl, alkenyl, arylalkenyl, heteroarylalkenyl, alkynyl, alkylcarbonyl, amido, alkylaminocarbonyl, arylaminocarbonyl, arylsulfonaminocarbonyl, carboxy, alkoxycarbonyl, arylcarbonyl, amino, alkylcarbonylamino, carbamoyl, alkylcarbamoyl, arylsulfonylamino, arylazo, hydroxy, alkoxy, haloalkoxy, arylalkoxy, alkylcarbonyloxy, arylcarbonyloxy, aryloxy, heteroaryloxy, thiol, alkylthio, arylthio, alkoxyarylthio, heteroarylthio, arylsulfinyl, cycloalkyl, heterocyclyl, aryl, aminocarbonylaryl, heteroaryl, and heteroarylheteroaryl;

wherein each amino substituent of each aryl is optionally substituted with 1 or 2 substituents independently selected from the group consisting of alkyl, aryloxyalkyl, arylthioalkyl, arylsulfinylalkyl, arylalkyl, heteroarylalkyl, arylalkenyl, heteroarylalkenyl, arylalkynyl, arylaminocarbonyl, arylsulfonaminocarbonyl, arylcarbonyl, arylazo, arylcarbonylamino, arylalkoxy, arylcarbonyloxy, aryloxy, heteroaryloxy, arylthio, alkoxyarylthio, heteroarylthio, arylsulfinyl, aryl, aminocarbonylaryl, heteroaryl, and heteroarylheteroaryl; and wherein each heteroaryl or heterocyclic aromatic is optionally substituted with 1, 2, 3, or 4 substituents independently selected from the group consisting of halogen, cyano, nitro, oxo, alkyl, carbalkoyl, arylalkyl, alkenyl, acyl, amido, alkylamido, carboxy, amino, alkanoylamino, arylcarbonylamino, hydroxy, alkoxy, aryloxy, thiol, alkylthio, cycloalkyl, aryl, heterocyclyl, and heteroaryl;

provided that the compound is not:

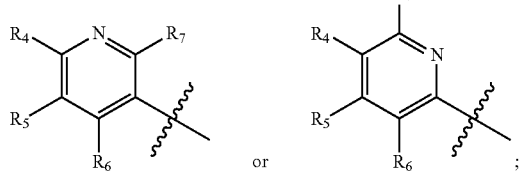

or

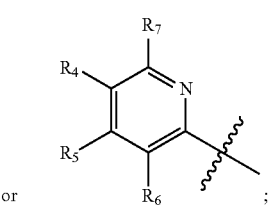

2. The method of claim 1, wherein:
Het is:

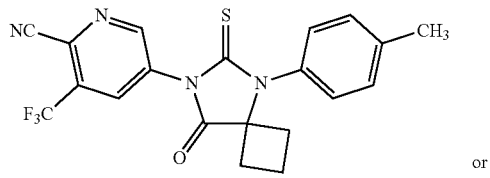

wherein:
R$_4$ is hydrogen, halogen, cyano, nitro, C$_{1-8}$ alkyl, or OR$_{11}$, wherein the C$_{1-8}$ alkyl is optionally substituted with 1 or more substituents independently selected from the group consisting of fluoro, chloro, bromo, and iodo;
R$_5$ is hydrogen, halogen, cyano, nitro, C$_{1-8}$ alkyl, or OR$_{11}$, wherein the C$_{1-8}$ alkyl is optionally substituted with 1 or more substituents independently selected from the group consisting of fluoro, chloro, bromo, and iodo;
R$_6$ is hydrogen, halogen, cyano, nitro, C$_{1-8}$ alkyl, or OR$_{11}$, wherein the C$_{1-8}$ alkyl is optionally substituted with 1 or more substituents independently selected from the group consisting of fluoro, chloro, bromo, and iodo; and
R$_7$ is hydrogen, halogen, cyano, nitro, C$_{1-8}$ alkyl, or OR$_{11}$, wherein the C$_{1-8}$ alkyl is optionally substituted with 1 or more substituents independently selected from the group consisting of fluoro, chloro, bromo, and iodo;
provided that R$_4$, R$_5$, R$_6$, and R$_7$ are not all hydrogen.

3. The method of claim 2, wherein Het is:

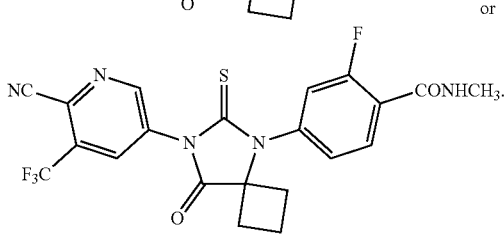

4. The method of claim 2, wherein:
(i) R$_4$ is cyano or nitro;
R$_5$ is hydrogen, halogen, C$_{1-8}$ alkyl, or OC$_{1-8}$ alkyl, wherein the C$_{1-8}$ alkyl and OC$_{1-8}$ alkyl are optionally substituted with 1 or more fluoro substituents;
R$_6$ is hydrogen; and
R$_7$ is hydrogen; or
(ii) R$_4$ is hydrogen, halogen, C$_{1-8}$ alkyl, or OC$_{1-8}$ alkyl, wherein the C$_{1-8}$ alkyl and OC$_{1-8}$ alkyl are optionally substituted with 1 or more fluoro substituents;
R$_5$ is cyano or nitro;
R$_6$ is hydrogen; and
R$_7$ is hydrogen.

5. The method of claim 2, wherein:
R$_4$ is cyano or nitro;
R$_5$ is hydrogen, halogen, C$_{1-8}$ alkyl, or OC$_{1-8}$ alkyl, wherein the C$_{1-8}$ alkyl and OC$_{1-8}$ alkyl are optionally substituted with 1 or more fluoro substituents;
R$_6$ is hydrogen; and
R$_7$ is hydrogen.

6. The method of claim 1, wherein R$_1$ is substituted phenyl.

7. The method of claim 1, wherein:
(i) R$_1$ is phenyl, substituted with 1 or more fluoro; or
(ii) R$_1$ is phenyl, substituted with 1 or more C$_{1-6}$ alkyl; or
(iii) R$_1$ is phenyl, substituted with 1 carbamoyl; or
(iv) R$_1$ is phenyl, substituted with 1 or more C$_{1-8}$ aklaminocarbonyl.

8. The method of claim 1, wherein R$_2$ and R$_3$, together with the carbon atom to which they are linked, form a C$_{3-6}$ cycloalkyl.

9. The method of claim 1, wherein R$_2$ and R$_3$, together with the carbon atom to which they are linked, form a cyclobutyl.

10. The method of claim 1, wherein the hyperproliferative disorder is prostate cancer.

11. The method of claim 1, wherein the hyperproliferative disorder is hormone refractory prostate cancer.

12. The method of claim 1, wherein the hyperproliferative disorder is hormone sensitive prostate cancer.

13. The method of claim 1, wherein the pharmaceutical composition is administered orally.

14. The method of claim 1, wherein the pharmaceutical composition is a unit dosage form comprising from 0.0005 mg to 500 mg of the compound of Formula II, or a pharmaceutically acceptable salt thereof, per unit dosage form.

15. The method of claim 1, wherein the pharmaceutical composition is administered daily to the patient in an amount to provide the patient with a dosage of the compound of Formula II, or a pharmaceutically acceptable salt thereof, in the range of from 0.01 mg per kg of body weight to 500 mg per kg of body weight.

* * * * *